US012630768B2

(12) United States Patent
Biber et al.

(10) Patent No.: US 12,630,768 B2
(45) Date of Patent: *May 19, 2026

(54) PURIFICATION OF WASTE PLASTICS BASED OIL VIA A POLYMERIZATION

(71) Applicant: TOTALENERGIES ONETECH, Courbevoie (FR)

(72) Inventors: Benjamin Biber, Exton, PA (US); Christine Richardson, Paris la Défense Cedex (FR); Delphine Minoux, Seneffe (BE); Keith Nelson, Aurora, CO (US); Cindy Adam, Seneffe (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/992,434

(22) PCT Filed: Jul. 13, 2023

(86) PCT No.: PCT/EP2023/069546
§ 371 (c)(1),
(2) Date: Jan. 8, 2025

(87) PCT Pub. No.: WO2024/013331
PCT Pub. Date: Jan. 18, 2024

(65) Prior Publication Data
US 2025/0257198 A1 Aug. 14, 2025

(30) Foreign Application Priority Data

Jul. 14, 2022 (EP) .................................... 22315146
Jul. 14, 2022 (EP) .................................... 22315147
(Continued)

(51) Int. Cl.
*C10G 1/10* (2006.01)
*B01D 3/14* (2006.01)
(Continued)

(52) U.S. Cl.
CPC ............... *C10G 1/10* (2013.01); *B01D 3/143* (2013.01); *B01D 15/08* (2013.01); *B01D 21/262* (2013.01);
(Continued)

(58) Field of Classification Search
CPC .............. C10G 1/10; C07C 2/06; B01D 3/143
See application file for complete search history.

(56) References Cited

U.S. PATENT DOCUMENTS 3,288,872 A 11/1966 House
3,911,041 A 10/1975 Kaeding et al.
(Continued)

FOREIGN PATENT DOCUMENTS

WO 2009092779 A2 7/2009
WO 2009092781 A2 7/2009
(Continued)

OTHER PUBLICATIONS

International Search Report and Written Opinion issued in Application No. PCT/EP2023/069546, dated Oct. 6, 2023, 9 pages.
(Continued)

*Primary Examiner* — Tam M Nguyen
(74) *Attorney, Agent, or Firm* — Ewing & Jones, PLLC

(57) ABSTRACT

The disclosure relates to the purification and treatment of oil produced from the liquefaction of waste polymer for instance the pyrolysis of waste plastics via the polymerization of dienes prior to further treatments.

16 Claims, 4 Drawing Sheets

(30) Foreign Application Priority Data

| | | | |
|---|---|---|---|
| Jul. 14, 2022 | (EP) | .................................... | 22315148 |
| Jul. 14, 2022 | (EP) | .................................... | 22315149 |
| Jul. 14, 2022 | (EP) | .................................... | 22315150 |
| Jul. 14, 2022 | (EP) | .................................... | 22315151 |
| Jul. 14, 2022 | (EP) | .................................... | 22315152 |
| Jul. 14, 2022 | (EP) | .................................... | 22315153 |

(51) Int. Cl.

| | |
|---|---|
| *B01D 15/08* | (2006.01) |
| *B01D 21/26* | (2006.01) |
| *B01D 36/04* | (2006.01) |
| *B01J 6/00* | (2006.01) |
| *B01J 19/06* | (2006.01) |
| *B01J 19/24* | (2006.01) |
| *B01J 29/00* | (2006.01) |
| *C07C 2/06* | (2006.01) |
| *C07C 2/38* | (2006.01) |
| *C07C 2/84* | (2006.01) |
| *C08J 11/12* | (2006.01) |
| *C08K 5/01* | (2006.01) |
| *C08L 9/06* | (2006.01) |
| *C08L 17/00* | (2006.01) |
| *C08L 21/00* | (2006.01) |
| *C09J 4/06* | (2006.01) |
| *C09J 11/08* | (2006.01) |
| *C09J 117/00* | (2006.01) |
| *C09J 121/00* | (2006.01) |
| *C10B 53/07* | (2006.01) |
| *C10B 57/14* | (2006.01) |
| *C10G 1/00* | (2006.01) |
| *C10G 7/00* | (2006.01) |
| *C10G 11/02* | (2006.01) |
| *C10G 19/02* | (2006.01) |
| *C10G 31/09* | (2006.01) |
| *C10G 31/10* | (2006.01) |
| *C10G 45/00* | (2006.01) |
| *C10G 50/00* | (2006.01) |
| *C10G 55/06* | (2006.01) |
| *C10G 63/04* | (2006.01) |
| *C10G 67/10* | (2006.01) |
| *C10G 69/12* | (2006.01) |

(52) U.S. Cl.

CPC ............ *B01D 36/045* (2013.01); *B01J 6/008* (2013.01); *B01J 19/06* (2013.01); *B01J 19/245* (2013.01); *B01J 29/00* (2013.01); *C07C 2/06* (2013.01); *C07C 2/38* (2013.01); *C07C 2/84* (2013.01); *C08J 11/12* (2013.01); *C08K 5/01* (2013.01); *C08L 9/06* (2013.01); *C08L 17/00* (2013.01); *C08L 21/00* (2013.01); *C09J 4/06* (2013.01); *C09J 11/08* (2013.01); *C09J 117/00* (2013.01); *C09J 121/00* (2013.01); *C10B 53/07* (2013.01); *C10B 57/14* (2013.01); *C10G 1/002* (2013.01); *C10G 7/006* (2013.01); *C10G 11/02* (2013.01); *C10G 19/02* (2013.01); *C10G 31/09* (2013.01); *C10G 31/10* (2013.01); *C10G 45/00* (2013.01); *C10G 50/00* (2013.01); *C10G 55/06* (2013.01); *C10G 63/04* (2013.01); *C10G 67/10* (2013.01); *C10G 69/126* (2013.01); *C08L 2207/20* (2013.01); *C08L 2207/324* (2013.01); *C10G 2300/1003* (2013.01); *C10G 2300/201* (2013.01); *C10G 2300/301* (2013.01); *C10G 2300/4006* (2013.01); *C10G 2400/04* (2013.01); *C10G 2400/20* (2013.01)

(56) References Cited

U.S. PATENT DOCUMENTS

| | | | |
|---|---|---|---|
| 4,639,259 A | 1/1987 | Pearson | |
| 4,762,537 A | 8/1988 | Fleming et al. | |
| 5,316,998 A | 5/1994 | Lee et al. | |
| 5,364,995 A | 11/1994 | Kirkwood et al. | |
| 5,505,926 A | 4/1996 | Lee et al. | |
| 5,573,990 A | 11/1996 | Wang et al. | |
| 5,639,937 A | 6/1997 | Hoever et al. | |
| 5,731,483 A | 3/1998 | Stabel et al. | |
| 6,797,851 B2 | 9/2004 | Martens et al. | |
| 8,895,790 B2 | 11/2014 | Narayanaswamy et al. | |
| 2014/0228606 A1 | 8/2014 | Narayanaswamy et al. | |
| 2021/0189250 A1 | 6/2021 | Timken | |
| 2023/0083199 A1* | 3/2023 | Jeon | C10G 65/043 |
| 2023/0083259 A1* | 3/2023 | Jeon | C10G 65/043 585/16 |
| 2024/0409824 A1* | 12/2024 | Jeon | B01J 8/0285 |
| 2025/0171695 A1* | 5/2025 | Biber | C10G 9/36 |
| 2025/0257273 A1* | 8/2025 | Biber | C10G 11/02 |

FOREIGN PATENT DOCUMENTS

| | | |
|---|---|---|
| WO | 2009098262 A1 | 8/2009 |
| WO | 2016009333 A1 | 1/2016 |
| WO | 2021204820 A1 | 10/2021 |

OTHER PUBLICATIONS

International Preliminary Report on Patentability issued in Application No. PCT/EP2023/069546, dated Oct. 17, 2024, 18 pages.

* cited by examiner

PURIFICATION OF WASTE PLASTICS BASED OIL VIA A POLYMERIZATION

CROSS-REFERENCE TO RELATED APPLICATIONS

This application claims the benefit of PCT/EP2023/069546 filed Jul. 13, 2023, which claims priority from EP 22315146.5, EP 22315147.3, EP 22315148.1, EP 22315149.9, EP 22315150.7, EP 22315151.5, EP 22315152.3, EP 22315153.1 all filed Jul. 14, 2022, which are incorporated herein by reference in their entireties for all purposes.

FIELD OF THE DISCLOSURE

The disclosure relates to the purification and treatment of oil produced from the liquefaction of waste polymers for instance the pyrolysis of waste plastic. In particular, the disclosure relates to the treatments that are performed on the oil obtained from the pyrolysis of plastic in order to be able to further use this oil in other processes such as for example in a steam cracker.

BACKGROUND OF THE DISCLOSURE

Waste plastics are mostly diverted to landfills or incinerated, with a smaller fraction being diverted to recycling. There is however a strong need, influenced by the regulations to limit waste plastics in landfills. On the other hand, waste plastics disposal in landfills is becoming increasingly difficult. There is therefore a need for better recycling of waste plastic.

A possible route to recycle plastic is via plastic pyrolysis. However, the pyrolysis plastic oil obtained from plastic pyrolysis generally contains large quantities of dienes. Those dienes react easily forming gums. Dienes are also coke precursors in a steam cracker.

In older documents, like U.S. Pat. Nos. 5,639,937, 5,731,483, and 5,364,995, the pyrolysis of waste plastics followed by the direct use of a steam cracker without any pretreatment before the steam cracker is described. However, due to the presence of dienes, the pyrolysis plastic oil cannot be used as such.

WO2021/204820 relates to a process for the purification of a hydrocarbon stream comprising the steps of providing a hydrocarbon stream having a diene value of at least 1.0, preferably at least 1.5 g $I_2$/100 g and a bromine number of at least 5 g $Br_2$/100 g and containing pyrolysis plastic oil; heating the stream obtained at a temperature of at most 230° C. followed by a mixing of the heated stream with a second diluent heated at a temperature of at least 300° C.; performing a hydroprocessing step at a temperature of at least 250° C. in the presence of $H_2$, and recovering a purified hydrocarbon stream. The process allows the dienes to be saturated.

U.S. Pat. No. 3,288,872 discloses a method for preparing polymers and copolymers of a conjugated diene such as 1,3-butadiene.

US 2021/0189250 provides a continuous process for converting waste plastic into recycle for polyethylene polymerization or for normal alpha olefins. The process comprises selecting waste plastics containing polyethylene and/or polypropylene and then passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char. The naphtha/diesel fraction is passed to a crude unit in a refinery from which is recovered a straight run naphtha fraction (C5-C8) or a propane/butane (C3-C4) fraction. The straight-run naphtha fraction, or propane and butane (C3-C4) fraction, is passed to a steam cracker for ethylene production. The ethylene is converted to normal alpha-olefin and/or polyethylene. Also, a heavy fraction from the pyrolysis reactor can be combined with a heavy fraction of the normal alpha olefin stream recovered from the steam cracker. The combined heavy fraction and the heavy fraction of normal alpha olefin stream can be passed to a wax hydrogenation zone to produce wax.

There is clearly a need for a process for purifying the pyrolysis plastic oil before use in a steam cracker. There is especially a need for removing the olefins and dienes.

SUMMARY OF THE DISCLOSURE

The aim of the present disclosure is to provide a process for the purification of liquified waste polymer. In particular, the aim of the present disclosure is to remove the dienes from the liquified waste polymer to be able to further convert this liquified waste polymer in other processes such as for instance a steam cracking reaction.

According to a first aspect, the disclosure provides a process for the purification of a liquified waste polymer comprising the following steps:

a) providing a feedstream containing liquified waste polymer, wherein said feedstream contains at least 0.1 wt. % to at most 80 wt. % of dienes based on the total weight of said feedstream;

c) performing a polymerization reaction on said feedstream under polymerization conditions to obtain a first product stream comprising an oligomeric product;

d) optionally, performing a neutralization reaction by contacting said first product stream with a basic compound to obtain a neutralized product stream and removing said basic compound from neutralized product stream to obtain a second product stream;

g) performing a separation to separate the oligomeric product from the purified liquified waste polymer.

It has been discovered that it is possible to have the dienes of a liquified waste polymer reacting via polymerization such as a cationic polymerization and hence forming heavier molecules or oligomeric products that are easily separated from the rest of the liquified waste polymer.

In some embodiments the liquified waste polymer is a pyrolysis plastic oil, with preference, the step a) of providing a feedstream containing liquified waste polymer comprises the preliminary steps of preparation of liquified waste polymer including:

a1) of providing a waste plastics stream;

a2) pyrolyzing said waste plastics stream at a temperature of at least 200° C.;

a3) recovering a pyrolizer effluent and separating, into a C1 to $C_4$ hydrocarbons fraction, a fraction having a boiling range higher than 350° C. and a remaining fraction being said pyrolysis plastic oil;

a4) optionally sending the fraction having a boiling range higher than 350° C. into a Fluid Catalytic Cracking (FCC) unit, or a hydrocracking unit, a coker or a visbreaker or blending said fraction having a boiling range higher than 350° C. in crude oil or in a crude oil cut to be further refined.

In an embodiment, the process further comprises a step (b) of drying the feedstream to obtain a dried feedstream wherein step b) is performed before step c) of polymerization so that step c) of polymerization reaction is performed on the dried feedstream.

For example, step b) of drying is performed and comprises a sub-step b1) of decantation and/or centrifugation; with preference, the first sub-step b1) is followed by a second sub-step b2) of drying using a molecular sieve to reach a water content of less than 0.1 vol. % according to ASTM D95-13 (2018).

The step c) comprises performing a polymerization reaction preferably a cationic polymerization or a free radical polymerization or an anionic polymerization.

In a preferred embodiment, the polymerization reaction is a cationic polymerization.

For example, the polymerization reaction in step c) is a cationic polymerization performed in the presence of an acidic catalyst; with preference, the acidic catalyst is a Brönsted acid or a Lewis acid; more preferably, the acidic catalyst is a Lewis acid.

For example, the polymerization reaction in step c) is a cationic polymerization performed in the presence of an acidic catalyst being a Lewis acid chosen among $BF_3$, complexes of boron trifluoride, $AlCl_3$, $SnCl_4$, $ZnCl_2$, $FeCl_3$ and $TiCl_3$, alkyl aluminum chlorides, $H_2SO_4$ or any mixture thereof; with preference, acidic catalyst is or comprises boron trifluoride etherate.

For example, the acidic catalyst is present at a concentration ranging from 0.5 wt. % to 5.0 wt. % based on the total weight of said feedstream and/or the polymerization reaction of step c) is carried out until the dienes of the purified liquified waste polymer are less than 5.0 wt. % based on the total weight of the first product stream.

In one or more embodiments, the polymerization conditions of step (c) comprise a contact time ranging from 5 min to 5 hours; and/or a temperature ranging from 5 to 100° C. at atmospheric pressure.

In some embodiments, the polymerization reaction of step c) is performed in the presence of one or more comonomers; with preference, the one or more comonomers comprise a vinyl aromatic and/or the one or more comonomers are present at a concentration from 1.0 to 25.0 wt. % based on the total weight of the liquified waste polymer.

In some embodiments, the basic compound forms a basic stream; wherein the basic stream and the first product stream are contacted with a weight ratio ranging from 1:1 to 1:1,000.

In embodiments wherein the polymerization is a cationic polymerization, step d) is performed and the concentration of the basic compound ranges from 0.1 to 50.0 wt. % based on the total weight of said neutralized product stream.

For example, the step d) is performed, and the basic compound:

has a pKa in water ranging from 7.5 to 14; and/or
is selected from LiOH, NaOH, CsOH, Ba(OH)$_2$, Na$_2$O, KOH, K$_2$O, CaO, Ca(OH)$_2$, MgO, Mg(OH)$_2$, NH$_4$OH or any mixtures thereof.

For example, step d) is performed in continuous mode, and/or step d) is performed and the removal of said basic compound from neutralized product stream to obtain a second product stream, is performed by decantation and/or by centrifugation.

In one or more embodiments, the process further comprises a step e) of washing the first product stream or the second product stream with a solvent to obtain a washed stream; with preference, the washing is performed at a temperature ranging from 5° C. to 95° C.

With preference, the solvent is selected from water or an aqueous acidic solution comprising:

one or more organic acids selected from citric acid ($C_6H_8O_7$), formic acid ($CH_2O_2$), acetic acid ($CH_3COOH$), sulfamic acid ($H_3NSO_3$) and any combination thereof and/or one or more inorganic acids selected from hydrochloric acid (HCl), nitric acid (HNO$_3$), sulfuric acid (H$_2$SO$_4$), phosphoric acid (H$_3$PO$_4$), and any combination thereof.

With preference, the washing is performed until the pH of said washed stream, is in the range of 5.0 to 9.0; the washing is followed by a decantation and/or a centrifugation to separate the solvent from washed stream.

In one or more embodiments, the process further comprises a step f) of filtering the stream obtained in the previous step to obtain a filtered stream wherein the filtering is performed to remove solids from the first product stream or from the second product stream or from the washed stream, and/or to coalesce remaining traces of solvent if any; with preference, the filtering step is followed by a dewatering step.

With preference, step g) of separation is performed via distillation, or steam distillation, or vacuum stripping, or fractional distillation, or any combination.

The oligomeric product obtained in the process can also be used further converted into valuable as valuable resins. In some embodiments, after the separation step g), the oligomeric product is recovered and mixed with an elastomer, a curing agent, and a filler to obtain a rubber composition or is used as a tackifying resin and mixed with an elastomer to form an adhesive composition.

In some embodiments, after the separation step g), the purified liquified waste polymer is recovered and blended in the fuel pool; with preference, the purified liquified waste polymer is separated in a naphtha cut having a boiling range of less than 150° C. and a diesel cut having a boiling range between 15° and 350° C. wherein said naphtha cut is incorporated in a naphtha pool, said diesel cut is incorporated in a diesel pool.

In some embodiments, after the separation step g), the purified liquified waste polymer is recovered and is further treated either pure or diluted in one or more of the following steps:

h) an optional purification step to trap silicon and/or metals and/or phosphorous and/or halogenates over at least one trap to obtain a purified stream; and/or i) an optional hydrotreating step of the purified stream or of said purified liquified waste polymer at a temperature of at least 200° C. to obtain a hydrotreated stream;

j) a steam cracking step of said hydrotreated stream or of said purified stream or of said purified liquified waste polymer to produce olefins such as ethylene and propylene and aromatics.

In some embodiments, after the separation step g), the purified liquified waste polymer is recovered and is further treated either pure or diluted in one or more of the following steps:

h) an optional purification step to trap silicon and/or metals and/or phosphorous and/or halogenates over at least one trap to obtain a purified stream; and/or k) a cracking step wherein said purified liquified waste polymer or said purified stream preferably diluted with a diluent, is cracked on a catalyst being a 10 MR or 12 MR molecular sieve at a temperature ranging from 450° C. to 650° C., a total pressure ranging from 0.5 to 10 barg and/or with a hydrogen partial pressure ranging from 0 to 7.5 barg to crack the olefins and/or paraffins of said purified liquified waste polymer into olefins having 2 to 4 carbon atoms.

In some embodiments, the liquified waste polymer in the feedstream has a final boiling point of at most 700° C. and/or the feedstream contains from 0.1 to 50.0 wt. % of dienes based on the total weight of said feedstream.

According to a second aspect, the disclosure provides an installation for carrying out a process for the purification of liquified waste polymer, said installation is remarkable in that it comprises:

a polymerization section;

an optional neutralization section;

a separation section;

wherein the polymerization section and the separation section are fluidically connected in series, and wherein the neutralization section when present is placed downstream of the polymerization section and upstream of the separation section.

With preference, the installation comprises:

a pre-treatment section comprising a pyrolysis unit, one or more separation units and an optional washing unit;

a drying section comprising a decanter and/or a centrifuge; and/or a molecular sieve;

a polymerization section comprising one or more polymerization reactors; preferably loaded with an acidic catalyst;

a neutralization section a mixing reactor and an optional separation unit comprising at least one selected from a decanter, a centrifuge, and a filter;

a washing section comprising a mixing vessel and a separation unit comprising a decanter and/or a centrifuge;

a filtering section comprising a filter and an optional molecular sieve.

a separation section comprising a separation unit comprising one or more distillation columns.

It is understood that the installation is configured to carry out the process according to the first aspect.

For example, the installation further comprises a purification section after the separation section.

For example, the installation further comprises a hydrotreating section and/or a steam cracking section.

For example, the installation further comprises a cracking section.

Definitions and Characterization Methods

For the purpose of the disclosure, the following definitions are given:

Weight hourly space velocity (WHSV) is defined as the hourly weight of flow per unit weight of catalyst and liquid hourly space velocity (LHSV) is defined as the hourly volume of flow per unit of volume of catalyst.

The terms "comprising", "comprises" and "comprised of" as used herein are synonymous with "including", "includes" or "containing", "contains", and are inclusive or open-ended and do not exclude additional, non-recited members, elements, or method steps. The terms "comprising", "comprises" and "comprised of" also include the term "consisting of".

The recitation of numerical ranges by endpoints includes all integer numbers and, where appropriate, fractions subsumed within that range (e.g., 1 to 5 can include 1, 2, 3, 4 when referring to, for example, a number of elements, and can also include 1.5, 2, 2.75 and 3.80, when referring to, for example, measurements). The recitation of endpoints also includes the recited endpoint values themselves (e.g., from 1.0 to 5.0 includes both 1.0 and 5.0). Any numerical range recited herein is intended to include all sub-ranges subsumed therein.

The term "conversion" means the mole fraction (i.e., percent) of a reactant converted to a product or products. The term "selectivity" refers to the percentage of converted reactants that went to a specified product.

The terms "wt. %", "vol. %", or "mol. %" refers to the weight, volume, or molar percentage of a component, respectively, based on the total weight, the total volume of material, or total moles, that includes the component. In a non-limiting example, 10 grams of a component in 100 grams of the material is 10 wt. % of component.

The term "naphtha" refers to the general definition used in the oil and gas industry. In particular, it refers to a hydrocarbon originating from crude oil distillation having a boiling range from 15 to 250° C. as measured by ASTM D2887-22e1. Naphtha contains substantially no olefins as the hydrocarbons originate from crude oil. It is generally considered that a naphtha has a carbon number between C3 and C11, although the carbon number can reach in some cases C15. It is also generally admitted that the density of naphtha ranges from 0.65 to 0.77 g/mL.

The term "gasoil" refers to the general definition used in the oil and gas industry. In particular, it refers to a hydrocarbon having a boiling point in the range of 250 to 350° C. as measured according to the ASTM D7500-15 (2019).

The term "liquified waste polymer" refers to any hydrocarbon liquid obtained from a waste polymer, preferably obtained from waste plastic. To obtain such liquified waste polymer, processes such as hydrothermal liquefaction or thermal pyrolysis or catalytic pyrolysis or steam pyrolysis, or even pyrolysis in the presence of hydrogen of waste polymer can be used. The waste polymers encompass any polymer that is considered as waste such as waste polyethylene (PE), waste polypropylene (PP), waste polyethylene terephthalate (PET), waste polyvinyl chlorine (PVC) but also other polymers originating from waste or used tires for instance. The term "liquified waste polymer" also encompasses "pyrolysis plastic oil".

The term "pyrolysis plastic oil" refers to the liquid products obtained once waste plastics have been thermally pyrolyzed. The pyrolysis process shall be understood as an unselective thermal cracking process. The pyrolysis involves the breaking of the polymer chains by heating. Rather than breaking the polymer down to its original monomers, pyrolysis tends to make a range of shorter-chain compounds, similar in many ways to the mixtures of hydrocarbons found in crude oil and oil products. A catalyst is sometimes used to reduce the operating temperature. The plastic being pyrolyzed can be of any type. For instance, the plastic being pyrolyzed can be polyethylene, polypropylene, polystyrene, polyesters, polyamides, polycarbonates, etc. These liquified waste polymers contain paraffins, i-paraffins (iso-paraffins), dienes, alkynes, olefins, naphthenes, and aromatic components. Liquified waste polymers may also contain impurities such as organic chlorides, organic silicon compounds, metals, salts, oxygenates, sulfur and nitrogen compounds, etc. The origin of the plastic is the waste plastics without limitation on the origin or on the nature of the plastic. The composition of the liquified waste polymer is dependent on the type of plastic pyrolyzed. It is however mainly constituted of hydrocarbons having from 1 to 50 carbon atoms and impurities.

The content in paraffin, naphthene, olefin, and aromatic is determined according to the standardized method UOP990-

11. This method uses two-dimensional gas chromatography (GCxGC) coupled with a flame ionization detector (FID).

The term Diene Value (DV) or Maleic Anhydride Value (MAV) corresponds to the amount of maleic anhydride (expressed as equivalents of iodine) which will react with 100 parts of oil under specific conditions. It is a measure of the conjugated double bonds in the oil. One mole of Maleic anhydride corresponds to 1 conjugated double bond. One known method to quantify the diene is the UOP 326-17: Diene Value by Maleic Anhydride Addition Reaction. The term diene value (DV) refers to the analytical method by titration expressed in g of iodine per 100 g of sample. The term Maleic Anhydride value (MAV) refers to the analytical method by titration expressed in mg of Maleic acid per g of sample. There is a correlation between the MAV=DV*3,863 since 2 moles of iodine correspond to 1 mole of Maleic Anhydride. For the examples presented, a particular method was used. The weight % of dienes presented in this application was obtained according to this particular method described in the example section.

The term bromine number corresponds to the amount of bromine in grams reacted by 100 grams of a sample. The number indicates the quantity of olefins in a sample. It is determined in grams of Br2 per 100 grams of solution (gBr2/100 g) and can be measured for instance according to the method ASTM D1159-07 (2017).

The term bromine index is the number of milligrams of bromine that react with 100 grams of sample. It is determined in milligrams of Br2 per 100 g of solution (mg Br2/100 g) and can be measured for instance according to the method ASTM D2710-20.

The term boiling point used refers to the boiling point generally used in the oil and gas industry. They are measured at atmospheric pressure. The initial boiling point is defined as the temperature value when the first bubble of vapor is formed. The final boiling point is the highest temperature that can be reached during a standard distillation. At this temperature, no more vapor can be driven over into the condensing units. The determination of the initial and the final boiling point is known per se in the art. Depending on the boiling range of the mixture they can be determined using various standardized methods such as for instance the ASTM D2887-22e1 relating to the boiling range distribution of petroleum fractions by gas chromatography. For compositions containing heavier hydrocarbons, the ASTM D7169-20 e1 can alternatively be used. The boiling ranges of the distillates can also advantageously be measured using the ASTM D7500-15 (2019) or the standard NF EN 15199-1. Due to the nature of the liquified waste polymer, the preferred method for the measurement of the boiling point is the method NF EN 15199-1. Depending on the method, up to 10° C. of difference can be evidenced. Hence, the boiling point expressed here is to be considered with an absolute uncertainty of +/−10° C.

The surface area and porous volume are measured via $N_2$ adsorption using usual surface area measurements. In particular, surface area measurements such as "BET" measurement can be used (i.e. ASTM D3663-20 for the surface area and D4365-19 for the porous volume). Other techniques well-known in the art can also be considered such as mercury adsorption techniques (ASTM D4284-12 (2017) e1). All measurements and data plots as utilized herein were made with a Micromeritics® Tristar 3000® analyzer. Surface Area: Total surface area was determined by $N_2$ sorption analysis according to ASTM D 4365-95 (reapproved 2008). Pore diameter and pore volume were determined according to D4641-94 (reapproved 2006).

The term MW stands for molecular weight, namely the mass of a compound divided by the amount of the compound in g/mol.

The concentration of metals in the matrix of hydrocarbon can be determined by any method known in the art. In particular, relevant characterization methods include XRF or ICP-AES methods. The man skilled in the art knows which method is the most adapted to each metal and to which hydrocarbon matrix.

The molecular weight: Mn (number average molecular weight), Mw (weight average molecular weight), Mz (z average molecular weight) and molecular weight distribution d (Mw/Mn) and d' (Mz/Mw) are determined by Gel Permeation Chromatography (GPC). The GPC was performed as follows.

Equipment: Agilent 1260 Series Degasser (Part Number G1322A); Agilent 1260 Series Isocratic Pump (Part Number G1310B); Agilent 1260 Series Autosampler (Part Number G1329B); Agilent 1260 Series Thermostatted Column Compartment (Part Number G1316A); Agilent 1260 Series Multiple Wavelength Detector (Part Number G1365C); and Agilent 1260 Series Refractive Index Detector (Part Number G1362A).

Column set: 1× Agilent ResiPore 50×4.6 m Guard Column (Part Number PL1513-1300); and 2× Agilent ResiPore 250×4.6 mm 3 um Particle Size Columns (Part Number PL1513-5300).
    Software: Cirrus 3.3, ChemStation B04.03[52].
    Solvent: THF Stabilized with 250 ppm BHT
    Flow Rate: 0.45 ml/min.
    Column Compartment Temperature: 40° C.
    Injection Volume: 5 ml
    Sample Preparation: Weighed approximately 0.06 grams of sample into a vial. Dissolve in 10 ml THF then filter through a 0.45 micron PTFE membrane. Run sample the same day it is prepared.
    Polystyrene calibration standard used.

The molecular weight averages used in establishing molecular weight/property relationships are the number average ($M_n$), weight average ($M_w$) and z average ($M_z$) molecular weight. These averages are defined by the following expressions and are determined from the calculated $M_i$:

$$M_n = \frac{\sum_i N_i M_i}{\sum_i N_i} = \frac{\sum_i W_i}{\sum_i W_i/M_i} = \frac{\sum_i h_i}{\sum_i h_i/M_i}$$

$$M_w = \frac{\sum_i N_i M_i^2}{\sum_i N_i M_i} = \frac{\sum_i W_i M_i}{\sum_i M_i} = \frac{\sum_i h_i M_i}{\sum_i M_i}$$

$$M_z = \frac{\sum_i N_i M_i^3}{\sum_i N_i M_i^2} = \frac{\sum_i W_i M_i^2}{\sum_i W_i M_i} = \frac{\sum_i h_i M_i^2}{\sum_i h_i M_i}$$

Here $N_i$ and $W_i$ are the number and weight, respectively, of molecules having molecular weight Mi.

The molecular weight distribution (MWD) is then calculated as $M_w/M_n$.

The crystallization temperature (Tc) and the glass temperature transition (Tg) were measured using differential scanning calorimetry (DSC), TA Instruments Q2000 equipped with a Liquid Nitrogen Cooling System (LNCS).

The software was TA Instruments Universal Analysis 2000 Version 4.5A. We used a temperature ramp with a ramp rate of 10° C./min.

The particular features, structures, characteristics, or embodiments may be combined in any suitable manner, as would be apparent to a person skilled in the art from this disclosure, in one or more embodiments.

DETAILED DESCRIPTION OF THE DISCLOSURE

Figure 1:
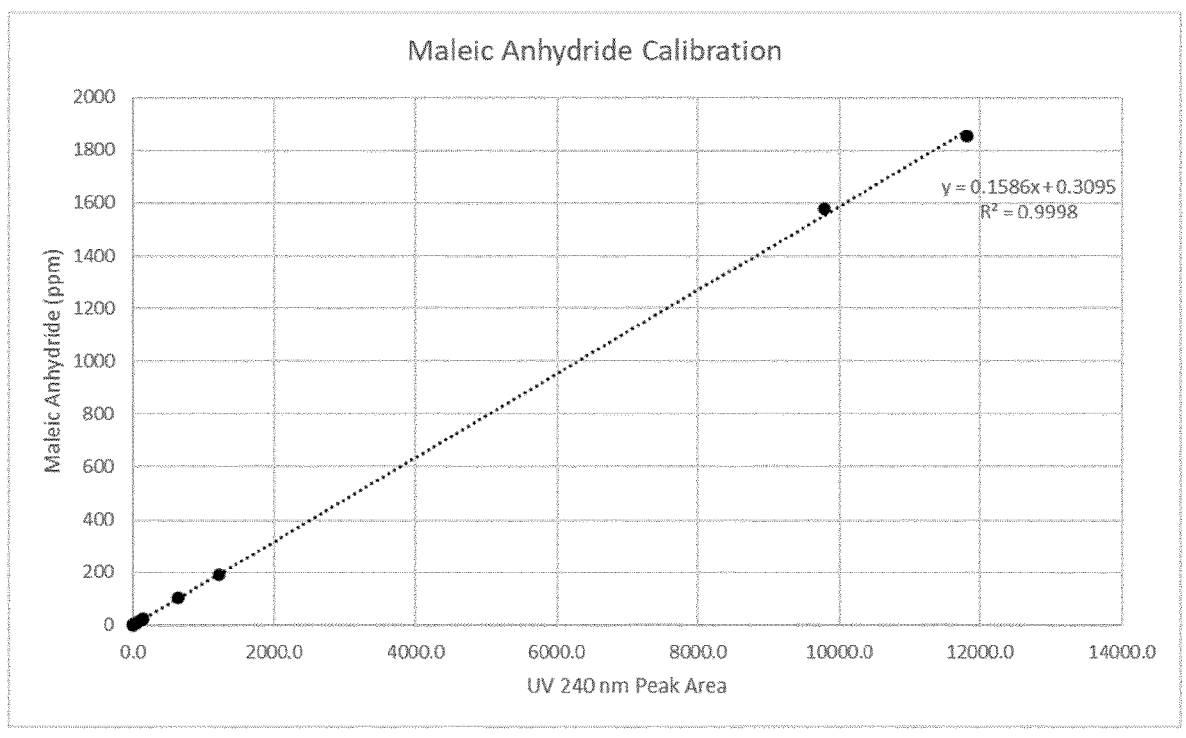
FIG. 1 calibration curve for maleic anhydride concentration versus UV signal.
Figure 2:
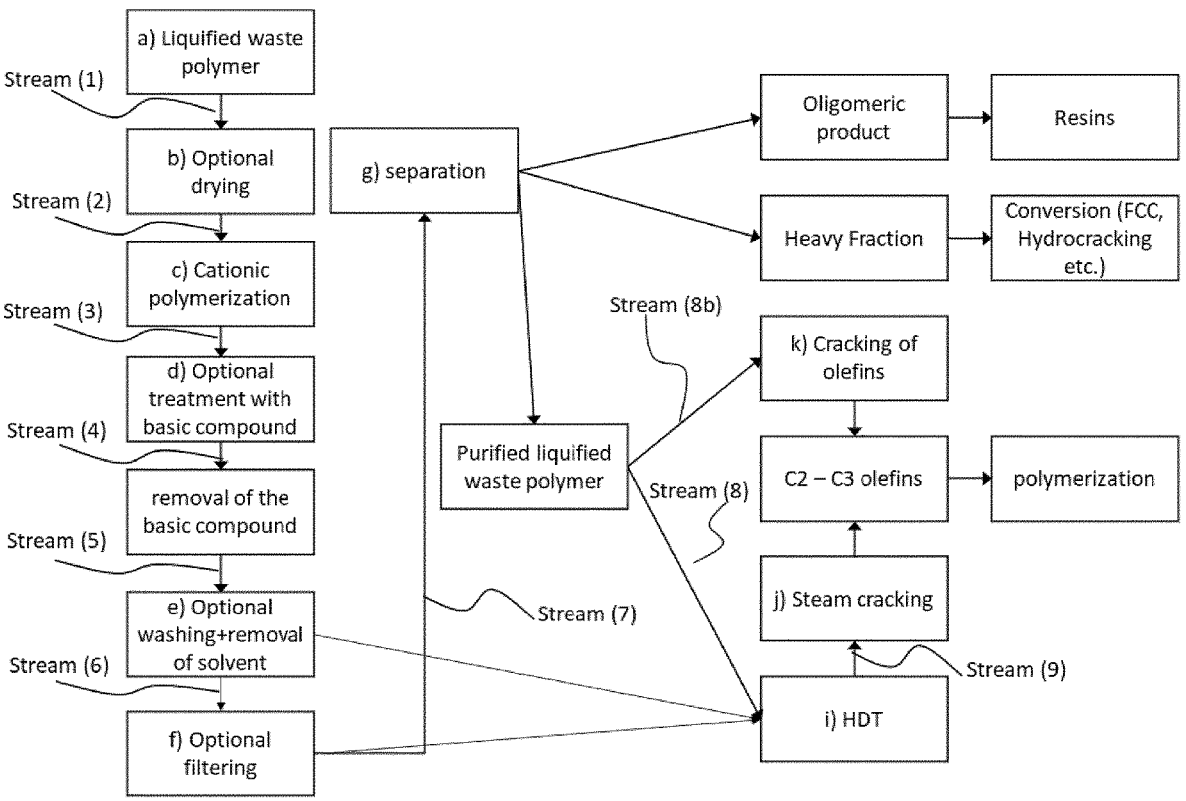
FIG. 2 describes a possible embodiment wherein the liquified waste polymer is firstly optionally dried, and sent to the cationic polymerization to convert the dienes into oligomeric products. The effluents of the cationic polymerization are then sent to an optional treatment with a basic compound followed by the removal of the basic compound and followed by an optional washing step. After an optional filtering step, the various fractions are separated into various fractions depending on the boiling point. If a heavy fraction can be separated, it is sent to conversion units. The oligomeric product that is converted into resins can also be separated. If a remaining fraction of purified plastic oil fraction is present it can be sent to a hydrotreatment or cracking or steam cracking to produce olefins being further polymerized.
Figure 5:
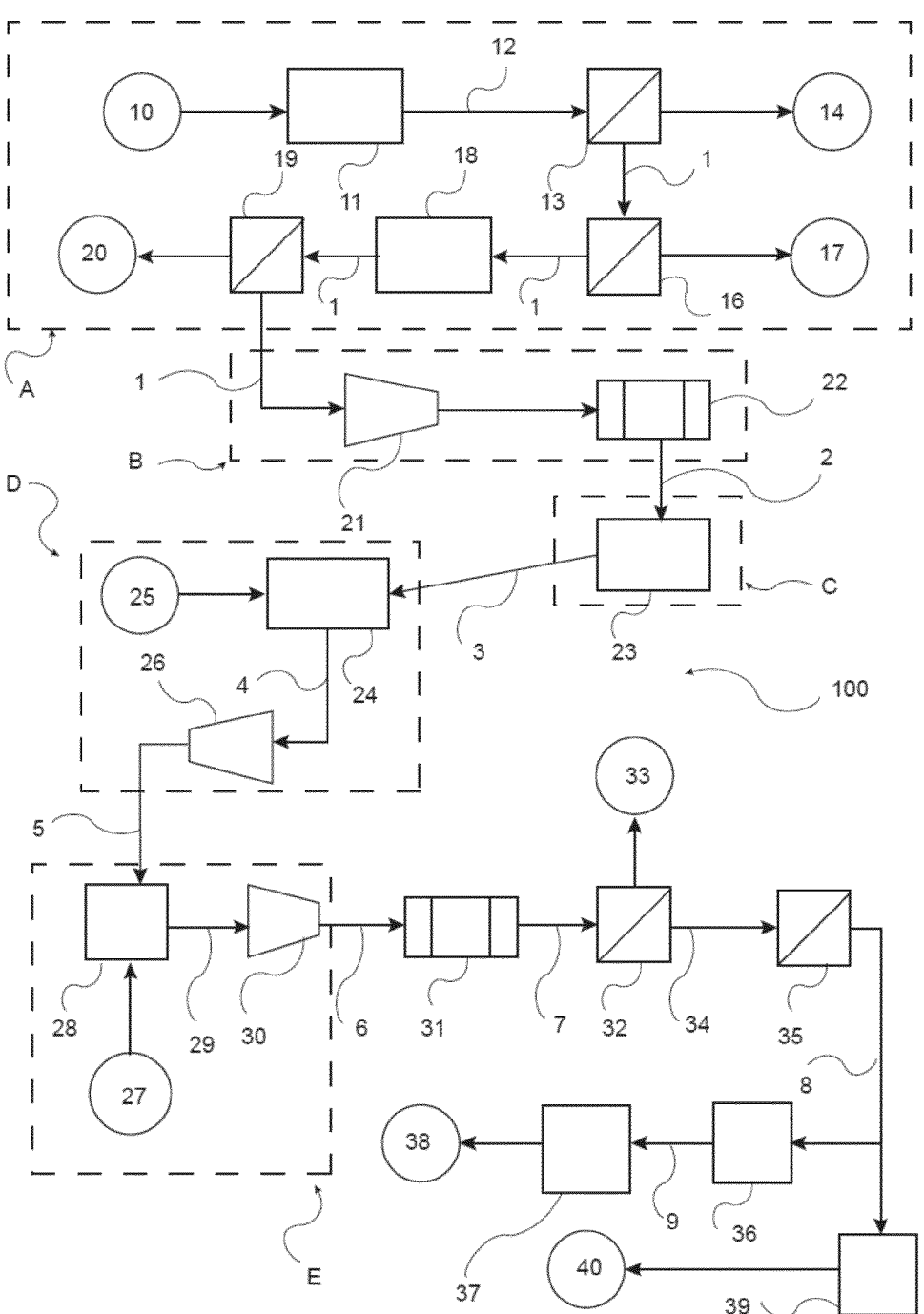
FIG. 5 is an example of an installation for carrying out the process of the disclosure.

The disclosure provides for a process and an installation for the purification of liquified waste polymer. Reference is made to FIG. 2 related to the process and FIG. 5 related to the installation. The installation and the process are described herein jointly.

The process for the purification of the liquified waste polymer according to the disclosure comprises the following steps:

a) providing a feedstream 1 containing liquified waste polymer, wherein said feedstream 1 contains at least 0.1 wt. % to at most 80 wt. % of dienes based on the total weight of said feedstream 1;

c) performing a polymerization reaction on said feedstream 1 under polymerization conditions to obtain a first product stream 3 comprising an oligomeric product;

d) optionally, performing a neutralization reaction by contacting said first product stream 3 with a basic compound to obtain a neutralized product stream 4 and removing said basic compound from neutralized product stream 4 to obtain a second product stream 5;

g) performing a separation to separate the oligomeric product from the purified liquified waste polymer.

In preferred embodiments illustrated in FIG. 2, the process for the purification of liquified waste polymer comprises the following steps:

a) providing a feedstream 1 containing liquified waste polymer, wherein said feedstream 1 contains at least 0.1 wt. % to at most 80 wt. % of dienes based on the total weight of said feedstream 1;

b) optionally, drying the feedstream 1 to obtain a dried feedstream 2;

c) performing a polymerization reaction on said feedstream 1 or on the dried feedstream 2 under polymerization conditions to obtain a first product stream 3 comprising an oligomeric product;

d) optionally, performing a neutralization reaction by contacting said first product stream 3 with a basic compound to obtain a neutralized product stream 4 and removing said basic compound from neutralized product stream 4 to obtain a second product stream 5;

e) optionally, washing the first product stream 3 or the second product stream 5 with a solvent to obtain a washed stream 6;

f) optionally, filtering the stream obtained in the previous step to obtain a filtered stream 7 wherein the filtering is performed to remove solids from the first product stream or from the second product stream 5 or from the washed stream 6, and/or to coalesce remaining traces of solvent if any;

g) performing a separation to separate the oligomeric product from the purified liquified waste polymer.

In a preferred embodiment, the process for the purification of the liquified waste polymer comprises the following steps:

a) providing a feedstream 1 containing liquified waste polymer, wherein said feedstream 1 contains at least 0.1 wt. % to at most 80 wt. % of dienes based on the total weight of said feedstream 1;

b) drying the feedstream 1 to obtain a dried feedstream 2;

c) performing a cationic polymerization reaction on the dried feedstream 2 under polymerisation conditions to obtain a first product stream 3 comprising an oligomeric product;

d) performing a neutralisation reaction by contacting said first product stream 3 with a basic compound to obtain a neutralized product stream 4 and removing said basic compound from neutralized product stream 4 to obtain a second product stream 5;

e) washing the second product stream 5 with a solvent to obtain a washed stream 6;

f) filtering the washed stream 6 to obtain a filtered stream 7 wherein the filtering is performed to remove solids from the washed stream 6, and/or to coalesce remaining traces of solvent if any;

g) performing a separation to separate the oligomeric product from the purified liquified waste polymer.

Whatever is the embodiment selected, after the separation step g), the purified liquified waste polymer may be recovered and be further treated either pure or diluted in one or more of the following steps:

h) an optional purification step to trap silicon and/or metals and/or phosphorous and/or halogenates over at least one trap to obtain a purified stream 8; and/or i) an optional hydrotreating step of purified stream 8 or of said purified liquified waste polymer at a temperature of at least 200° C. to obtain a hydrotreated stream 9;

j) a steam cracking step of said hydrotreated stream 9 or of said purified stream 8 or of said purified liquified waste polymer to produce olefins such as ethylene and propylene and aromatics.

Alternatively, after the separation step g), the purified liquified waste polymer may be recovered and be further treated either pure or diluted in one or more of the following steps:

h) an optional purification step to trap silicon and/or metals and/or phosphorous and/or halogenates over at least one trap to obtain a purified stream 8; and/or k) a cracking step wherein said purified liquified waste polymer or said purified stream 8 being preferably diluted with a diluent, is cracked on a catalyst being a 10 MR or 12 MR molecular sieve at a temperature ranging from 450° C. to 650° C., a total pressure ranging from 0.5 to 10 barg and/or with a hydrogen partial pressure ranging from 0 to 7.5 barg to crack the olefins and/or paraffins of said purified liquified waste polymer into olefins having 2 to 4 carbon atoms.

The disclosure also provides an installation 100 for carrying out a process for the purification of liquified waste polymer, said installation is remarkable in that it comprises:

a polymerization section C comprising one or more polymerization reactors 23;

an optional neutralisation section D;

a separation section comprising a separation unit 32 comprising one or more distillation columns.

wherein the polymerization section C and the separation section are fluidically connected in series, and wherein the neutralization section D when present is placed downstream of the polymerization section and upstream of the separation section.

In some embodiments, the disclosure also provides an installation 100 for carrying out a process for the purification of liquified waste polymer, said installation is remarkable in that it comprises, fluidically connected in the given order:

an optional pre-treatment section A;

an optional drying section B;

a polymerization section C comprising one or more polymerisation reactors 23;

an optional neutralisation section D;

an optional washing section E;

an optional filtering section; and a separation section comprising a separation unit 32 comprising one or more distillation columns.

In an embodiment, the disclosure also provides an installation 100 for carrying out a process for the purification of liquified waste polymer, said installation is remarkable in that it comprises:

a pre-treatment section A comprising a pyrolysis unit 11, one or more separation units (13, 16, 19) and an optional washing unit 18;

a drying section B comprising a decanter and/or a centrifuge 21; and/or a molecular sieve 22;

a polymerization section C comprising one or more polymerization reactors 23; preferably loaded with an acidic catalyst;

a neutralization section D a mixing reactor 24 and an optional separation unit 26 comprising at least one selected from a decanter, a centrifuge, and a filter;

a washing section E comprising a mixing vessel 28 and a separation unit 30 comprising a decanter and/or a centrifuge;

a filtering section comprising a filter and an optional molecular sieve 31; and a separation section comprising a separation unit 32 comprising one or more distillation columns.

The Feedstream 1 and Step a) of Providing a Feedstream 1 and the Pretreatment Section A The feedstream 1 used in the process contains a liquified waste polymer.

It is preferred that the liquified waste polymer is originated from the pyrolysis of plastic waste 10, so that the liquified waste polymer is a pyrolysis plastic oil.

Thus, in a preferred embodiment, step a) of providing a feedstream 1 comprises the preliminary steps of preparation of liquified waste polymer including:

a1) providing a waste stream 10 being preferably a waste plastics stream;

a2) pyrolyzing said waste stream 10 at a temperature of at least 200° C.;

a3) recovering a pyrolizer effluent 12 and separating said pyrolizer effluent into a C1 to C4 hydrocarbons fraction 14, a fraction 17 having a boiling range higher than 350° C. and a remaining fraction being said pyrolysis plastic oil.

In such cases, the installation 100 may comprise a pretreatment section A comprising a pyrolysis unit 11, one or more separation units (13, 16, 19) and an optional washing unit 18. With preference, the pretreatment section A comprises one or more separation units selected from:

a first separation unit 13 to remove pyrolysis gas comprising a gas-liquid separator a second separation unit 16 to remove the fraction having a boiling range higher than 350° C. comprising one or more distillation columns; and a third separation unit 19 to remove particles and gums, comprising a filter and/or a centrifuge In some embodiments (not illustrated) the process further comprises a further preliminary step of treatment of the fraction having a boiling range higher than 350° C. and therefore further comprises a step a4) of sending said fraction having a boiling range higher than 350° C. into a Fluid Catalytic Cracking (FCC) unit, or a hydrocracking unit, a coker or a visbreaker; or of blending said fraction having a boiling range higher than 350° C. in crude oil or in a crude oil cut to be further refined.

In a preferred embodiment, the liquified waste plastics comprise mainly pyrolysis plastic oil. Pyrolysis plastic oil is produced from plastic wastes that are pyrolyzed. An example of a pyrolysis process for waste plastics is disclosed in U.S. Pat. No. 8,895,790 or in US 2014/228606 and in WO2016/009,333.

In a waste plastics pyrolyzer, mixed plastics (e.g., waste plastics 10) are placed in a pyrolysis unit or pyrolyzer. In the pyrolysis unit 11, the waste plastics are converted via pyrolysis to a pyrolysis product, wherein the pyrolysis product 12 comprises a gas phase (e.g., pyrolysis gases, such as C1 to C4 gases, hydrogen ($H_2$), carbon monoxide (CO), carbon dioxide ($CO_2$) mainly) and a liquid phase being pyrolysis plastic oil.

The plastic waste 10 may include post-consumer waste plastics, such as mixed plastic waste. Mixed plastics can comprise non-chlorinated plastics (e.g., polyolefins, polyethylene, polypropylene, polystyrene, copolymers, etc.), chlorinated plastics (e.g., polyvinylchloride (PVC), polyvinylidene chloride (PVDC), etc.), and the like, or mixtures thereof. Generally, waste plastics 10 comprise long-chain molecules or polymer hydrocarbons. Waste tires may also be used. Namely waste plastics may also include used tires.

The pyrolysis unit 11 may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation.

The vessel may contain one or more beds of inert material or a pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit. Alternatively, the pyrolysis unit 11 can be operated without any catalyst (e.g., pure thermal pyrolysis).

The pyrolysis unit 11 may be operated adiabatically, isothermally, nonadiabatically, non-isothermally, or combinations thereof. The pyrolysis reactions of this disclosure may be carried out in a single stage or in multiple stages. For example, the pyrolysis unit 11 can be two reactor vessels fluidly connected in series.

In a configuration (not illustrated) where the pyrolysis unit comprises two vessels, the pyrolysis process may be divided into a first stage which is performed in a first vessel, and in a second stage fluidly connected downstream to the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit 11 may include one or more equipments configured to convert mixed plastics into gas phase and liquid phase products. The one or more equipments may or may not contain an inert material or pyrolysis catalyst as described above. Examples of such equipment include one or more of heated extruders, heated rotating kilns, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit 11 can be configured to pyrolyze (e.g., crack), and in some aspects (e.g., where hydrogen is added to the pyrolysis unit), additionally hydrogenate components of the waste plastics stream fed to the pyrolysis unit. Examples of reactions that may occur in the pyrolysis unit 11 include but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit 11, a headspace purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The headspace purge gas may include hydrogen (H2), C1 to C4 hydrocarbon gases (e.g., alkanes, methane, ethane, propane, butane, isobutane), inert gases (e.g., nitrogen ($N_2$), argon, helium, steam), and the like, or combinations thereof. The use of a headspace purge gas assists in the dechlorination in the pyrolysis unit when the waste plastics comprise chlorinated plastics. The headspace purge gas may be introduced to the pyrolysis unit to aid in the removal of volatiles entrained in the melted mixed plastics present in the pyrolysis unit.

A hydrogen ($H_2$) containing stream can be added to the pyrolysis unit 11 to enrich the pyrolysis unit environment with $H_2$, assist in stripping entrapped hydrogen chloride in the pyrolysis unit, provide a local environment rich in hydrogen in the pyrolysis melt or liquid, or combinations thereof; for example, via an $H_2$ containing stream fed directly to the pyrolysis unit 11 independently of the waste plastics 10 stream. In some aspects, $H_2$ can also be introduced along with a stream to the pyrolysis unit 11, with adequate safety measures incorporated for hydrogen handling with plastics feed.

The pyrolysis unit 11 may facilitate any reaction of the components of the waste plastics 10 stream in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally, or alternatively, reactions in the pyrolysis unit may cause a rupture of a bond of an organic compound, with a subsequent reaction and/or replacement of a heteroatom with hydrogen.

The use of hydrogen in the pyrolysis unit 11 can have beneficial effects of (I) reducing the coke as a result of cracking, (II) keeping the catalyst used (if any) in the process in an active condition, (III) improving removal of chloride from a stream such that the pyrolysis product from pyrolysis unit 11 is substantially dechlorinated with respect to waste plastics stream, which minimizes the chloride removal requirement in units downstream of the pyrolysis unit, (IV) hydrogenating of olefins, (V) reducing diolefins in pyrolysis product, (VI) helping operate the pyrolysis unit 11 at reduced temperatures for same levels of conversion of waste plastics 10 stream in the pyrolysis unit, or combinations of (I)-(VI).

The pyrolysis processes in the pyrolysis unit 11 may be low severity or high severity.

Low-severity pyrolysis processes may occur at a temperature of less than about 450° C.; for example, at a temperature ranging from 250° C. to 450° C., preferably from 275° C. to 425° C., more preferably 300° C. to 400° C., and may produce pyrolysis oils rich in mono- and di-olefins as well as a significant amount of aromatics.

High-severity pyrolysis processes may occur at a temperature equal to or greater than about 450° C.; for example, at a temperature ranging from 450° C. to 750° C., preferably from 500° C. to 700° C., more preferably from 550° C. to 650° C., and may produce pyrolysis oils rich in aromatics, as well as more gas products (as compared with low severity pyrolysis).

As will be appreciated by one of skill in the art, a high severity pyrolysis process will lead to the formation of more olefins and diolefins. Those olefins and diolefins cannot easily be recovered.

A pyrolysis product 12 can be recovered as an effluent from the pyrolysis unit 11 and conveyed (e.g., flowed, for example via pumping, gravity, pressure differential, etc.) to a pyrolysis separating unit (i.e., a first separation unit 13). The pyrolysis product 12 can be separated in the pyrolysis separating unit into a pyrolysis gas 14 stream and a pyrolysis plastic oil further used in step a) of the present disclosure.

The first separation unit 13 may comprise any suitable gas-liquid separator, such as a vapor-liquid separator, oil-gas separators, gas-liquid separators, degassers, scrubbers, traps, flash drums, compressor suction drams, gravity separators, centrifugal separators, filter vane separators, mist eliminator pads, liquid-gas coalescers, distillation columns, and the like, or combinations thereof.

In a preferred embodiment, said of pyrolysis plastic oil originates directly from the pyrolysis of plastic wastes without further chemical transformation or separation.

In a preferred embodiment, the feedstream 1 contains only liquified waste polymer even more preferably only pyrolysis plastic oil. Alternatively, the feedstream 1 contains at least 10 wt. % of liquified waste polymer based on the total weight of the feedstream 1; preferably at least 25 wt. %, more preferably at least 50 wt. %, even more preferably at least 75 wt. %.

The feedstream 1 may contain 100 wt. % of said liquified waste polymer based on the total weight of the feedstream 1; preferably at most 95 wt. %; more preferably, at most 90 wt. %; even more preferably at most 85 wt. %, and most preferably at most 80 wt. %. When the feedstream 1 contains less than 100 wt. % of liquid waste polymer the rest can be for instance a diluent or other hydrocarbons.

In a preferred embodiment, the feedstream 1 presents a bromine number of at most 150 g $Br_2$/100 g as measured according to ASTM D1159-07(2017), preferably at most 100 g $Br_2$/100 g; more preferably at most 80 g $Br_2$/100 g, and even more preferably, at most 50 g $Br_2$/100 g.

In a preferred embodiment, the liquified waste polymer in the feedstream 1 has a starting boiling point of at least 15° C. and a final boiling point of at most 700° C. With preference, the final boiling point is at most 600° C.; more preferably 560° C., even more preferably 450° C. even more preferably 350° C., the most preferred 250° C.

In some embodiment, step a) of providing a feedstream 1 comprises one or more sub-steps of pre-treatment of the liquified waste polymer.

Indeed, depending on the origin of the liquified waste polymer, some pre-treatment may be necessary. Namely, before purifying the liquified waste polymer in the inventive process, the following pre-treatment may be considered either on the liquified waste polymer or on the feedstream 1.

In a preferred embodiment, the liquified waste polymer or the feedstream 1 is pretreated in a washing or a desalting unit 18 to remove water-soluble salts before being treated in the inventive process.

In another preferred embodiment, the liquified waste polymer or the feedstream 1 is pretreated in a separation unit 19 to extract the particles and gums 20 by filtration, centrifugation or a combination of the two technics before being treated in the inventive process.

The Optional Step b) of Drying the Feedstream 1 to Obtain a Dried Feedstream 2 and the Drying Section B In another preferred embodiment, the liquified waste polymer or the feedstream 1 may be pretreated in a dewatering unit (i.e., a drying unit) to remove water and reach a water content of less than 0.1 vol. % preferably of less than 0.05% vol according to ASTM D95-13 (2018) before being treated in the inventive process, even more preferably said liquified waste polymer may be decanted.

Preferably, the feedstream 1 is dried before being sent to the polymerisation unit. the step b) of drying can be performed a sub-step b1) of decantation and/or centrifugation; with preference, the sub step b1) is followed by a sub-step b2) of drying using a molecular sieve 22 to reach a water content of less than 0.1 vol. % according to ASTM D95-13 (2018).

In such cases, the installation 100 may comprise a drying section B comprising:

a decanter and/or a centrifuge 21; and/or a molecular sieve 22

The Step c) of Performing a Polymerization Reaction on the Feedstream 1 or the Dried Feedstream 2 and the Polymerization Section C The step c) comprise performing a polymerization reaction being a cationic polymerization or a free radical polymerization or an anionic polymerization; with preference, the polymerization reaction is a cationic polymerization. Thus, the polymerization section C comprises one or more polymerization reactors 23 loaded with a catalyst; preferably an acidic catalyst.

In an embodiment, said polymerization is an anionic polymerization. In such case, said anionic polymerization is performed using an organolithium containing anionic initiator and terminated by reaction with a proton donating termination agent selected to form the lithium salt which can be filtered.

In the embodiments wherein the polymerization reaction is a cationic polymerization, the installation comprises a polymerization section C comprising one or more polymerization reactors 23 loaded with an acidic catalyst.

In another embodiment, said polymerization is a free radical polymerization. In such case, said free radical polymerization is performed with an initiator utilized to generate an initial radical leading to monomer propagation followed by a termination via combination or disproportionation.

In preferred embodiments, the polymerization reaction is a cationic polymerization. Thus, preferably, step c) is performed in the presence of an acidic catalyst; with preference, the acidic catalyst is a Brönsted acid or a Lewis acid; preferably a Lewis acid in the form of a transition metal halogenate.

Friedel-Crafts catalysts are Lewis acid catalysts that polymerize monomers via a cationic polymerization reaction mechanism. According to various embodiments, examples of Friedel-Crafts catalysts that may be used to polymerize a monomer feed comprising pyrolysis oil include, but are not limited to, boron trifluoride, aluminum trichloride, tin tetrachloride, titanium trichloride, titanium tetrachloride, iron chloride (III), aluminum tri-bromide, dichloromono ethyl aluminum, and complexes thereof, such as boron trifluoride—phenol complex, boron trifluoride—ethanol complex, boron trifluoride—ether complex and the like, especially, boron trifluoride—phenol complex and boron trifluoride—ethanol complex. The Friedel-Craft catalyst may also include a liquid aluminum chloride/hydrochloric acid/substituted aromatics complex, the aromatic being for example o-xylene, mesitylene, ethyl benzene, isopropyl benzene, and the like, such as short or long-chain alkylbenzenes. The alky chain may be linear or branched and may vary from 2 to 30 carbon atoms. Acidic liquid AlCl, obtained as by-products during the alkylation of benzene or any other substituted aromatics (toluene, xylenes) with branched-chain olefins may also be used. The branched-chain olefins may be produced via the boron trifluoride oligomerization of propylene and fractionation (e.g. C12 olefins or C24 olefins may be alkylated with aromatics).

The Friedel—Crafts catalysts most preferred are $AlCl_3$ and $BF_3$.

Thus, with preference, the step c) is performed in the presence of an acidic catalyst being a Lewis acid chosen among $BF_3$, complexes of boron trifluoride, $AlCl_3$, $SnCl_4$, $ZnCl_2$, $FeCl_3$ and $TiCl_3$, alkyl aluminum chlorides, $H_2SO_4$ or any mixture thereof. It is understood that $BF_3$ refers to $BF_3$ in the gaseous form. A particularly suitable complex of boron trifluoride is boron trifluoride etherate.

In an embodiment, step c) is performed in the presence of an acidic catalyst being a Lewis acid with an acidic catalyst concentration ranging from 0.5 wt. % to 5.0 wt. % based on the total weight of said feedstream 1.

In an embodiment, the reaction conditions include a contact time of at least 5 min to at most 5 hours. Preferably, step c) is performed under an inert atmosphere, preferably under $N_2$ atmosphere.

The resins described herein may be prepared by a continuous solution polymerization process wherein the Friedel-Craft catalyst, optional comonomers, and a suitable aromatic or aliphatic hydrocarbon solvent, such as, for example, toluene, xylene, or heptane, are continuously added to a reactor vessel to form the desired homopolymer or copolymer. Alternatively, the pyrolysis oil-based polymers may be prepared through a batch process in which all the initiator, monomers, and solvent are combined in the reactor together and mixed. The acid catalyst may also be a solid catalyst.

Preferably, during a continuous polymerization reaction, the mass flow rate of the catalyst feed is from 0.01 to 20 wt. % based on the total mass flow rate of monomer feed and catalyst feed; preferably, from 0.1 to 5 wt. %, and more preferably from 0.1 to 3 wt. %.

The reaction temperature of the mixture in the reactor vessel is also preferably maintained at a temperature of about −10 to 50° C., when using BF, as the Friedel-Crafts catalyst and about 10 to 60° C., when using $AlCl_3$.

The low molecular weight pyrolysis oil-based homopolymers or copolymers resins according to the embodiments are liquid resins with a number average molecular weight between 100 and 10,000 g/mol and more preferably 250 and 4,000 g/mol, as measured via gel permeation chromatography and converted using polystyrene calibration.

In a preferred embodiment, the cationic polymerization is performed in the presence of an acidic catalyst, being preferably chosen among $BF_3$, $AlCl_3$, $SnCl_4$, and $TiCl_3$, ion exchange resin, $Cl_2AlEt$, $H_2SO_4$ or any mixture thereof.

In an embodiment, at least one of $AlCl_3$, and $BF_3$, may be used to polymerize a monomer feed comprising pyrolysis oil and a comonomer in which the comonomer content of the monomer feed is <90 wt. %, <40 wt. %, <25 wt. %, or <15 wt. %, based on the total moles of the monomer in the monomer feed. Preferably, the polymerization initiator is $BF_3$.

In particular, the acidic catalyst can be a solid acidic catalyst. The preferred solid acid catalyst includes molecular sieves such as zeolite or silicalite. The use of a solid acidic catalyst is particularly advantageous. The solid acid catalyst can be easily separated. When a solid acid catalyst is used, the use of a neutralization step d) and the step of washing e) may not be required.

In an embodiment, step c) is performed with a solid acid catalyst being a molecular sieve, preferably selected among the topologies MFI, BEA, FAU, MEL, and the polymerization conditions comprise a Liquid Hourly Space Velocity (LHSV) ranging from 0.5 to 5.0 $h^{-1}$. In a preferred embodiment, the molecular sieve contains one or more heteroatoms selected from Ti, Sn, Mo, W, Fe, Ni, Co, Cu, Zr, Hf, Nb, and Ta.

In an embodiment, step c) is performed with a solid acid catalyst being an ion exchange resin, preferably a sulfonic ion-exchange resin such as Amberlyst A15 or A35, and the polymerization conditions comprise an LHSV ranging from 0.5 to 5.0 $h^{-1}$. Ion exchange resin includes macro-porous polymeric resins having acidic properties for instance having the capability to exchange $H^+$ ions. In particular, ion exchange resins can comprise styrene-divinylbenzene copolymers such as for instance Amberlyst resins. In a preferred embodiment, the ion exchange resin is an Amberlyst 15.

In an embodiment, step c) is performed with a solid acid catalyst being a clay or an activated clay and the polymerization conditions comprise an LHSV ranging from 0.5 to 5.0 $h^{-1}$.

The Optional Neutralization Step d) and the Neutralization Section D

When an acidic catalyst soluble is used in step c) to produce the first product stream 3, it may be required to perform a neutralization step d1) preferably followed by a washing step d2).

Thus, in some embodiments, the installation 100 comprises a neutralization section D comprising a mixing reactor 24 and an optional separation unit 26 comprising at least one selected from a decanter, a centrifuge, and a filter.

The step d) is a neutralization step that can be done by adding a base directly on said first product stream 3. In that case, a basic compound 25, generally solid is put in contact with said first product stream 3, the mixture obtained is then agitated for at least 1 second to at most 24 h, preferably during at least 1 minute to at most 12 h. After agitation, the remaining base in the form of a solid is separated from the liquid, said liquid being said second product stream 5.

The neutralization step can also be done by washing said first product stream with a basic compound 25 being a basic solution. Basic aqueous solutions are preferred, basic aqueous solutions containing NaOH and/or $NH_4OH$ are the most preferred type of solution. The basic solutions are put in contact and agitated for at least 1 second to at most 24 h, preferably for at least 1 minute to at most 12 h. Then the mixture is let for separation to remove the second product stream 5 (being the organic phase) from the aqueous phase. The separation can consist for instance in a decantation. The decantation is known per se, it consists in letting the immiscible organic and aqueous phases be separated with the help of gravity.

The neutralization step can also be done by putting simultaneously or successively one or more basic compounds 25, preferably a base containing alkali/alkaline earth metals, more preferably a solid base such as LiOH, NaOH, CsOH, $Ba(OH)_2$, $Na_2O$, KOH, $K_2O$, CaO, $Ca(OH)_2$, MgO, $Mg(OH)_2$ or any mixture thereof or any strong base alone or in mixture, and a basic aqueous solution in contact with said first product stream 3. After agitation of at least 1 second to at most 24 h, the solid, the organic phase being said second product stream 5, and the aqueous phase are separated.

In a more preferred embodiment, the step d) is performed in continuous mode, namely the addition of fresh basic compound is performed on the first product stream 3 at the entry of for instance a mixing reactor 24 while simultaneously, at the exit of the mixing reactor 24 the spent basic compound is removed to obtain the second product stream 5.

In a preferred embodiment, the basic compound comprises an alkali metal cation, alkaline earth metal cation, and ammonium quaternary base, being preferably chosen among TMAOH, TEAOH, TBAOH, TPAOH, or any mixture thereof.

The Optional Washing Step e) and the Washing Section E

The washing step e) comprises washing the first product stream 3 or the second product stream 5 with a solvent 27 to obtain a washed stream 6. In some embodiments, the washing step e) is performed after the neutralization step d) to remove traces of the basic compound 25. In such a case, the washing step is performed with a ratio of said second product stream 5, or optionally of said neutralized product stream 4, over said solvent 27 ranging from 0.05 to 20.

For example, the washing is performed at a temperature ranging from 5° C. to 95° C., preferably under atmospheric pressure. The washing can be performed in continuous mode or in batch mode.

In a preferred embodiment, the solvent is selected water or an acidic water solution, said solution comprising one or more organic acids like for instance citric acid ($C_6H_8O_7$), formic acid ($CH_2O_2$), acetic acid ($CH_3COOH$), sulfamic acid ($H_3NSO_3$) or inorganic acids being hydrochloric acid (HCl), nitric acid ($HNO_3$), sulfuric acid ($H_2SO_4$), phosphoric acid ($H_3PO_4$) and any combination thereof.

For example, the acidic solution has a pH ranging from 0.1 to 6.9.

The washing is preferably performed until the pH of said washed stream 6, or optionally on said second product stream 5, or neutralized product stream 4, is in the range of 5.0 to 9.0, preferably in the range of 6.0 to 8.0, even more preferably in the range of 6.5 to 7.5.

The washing is preferably followed by a decantation and/or a centrifugation to separate the solvent 27 from the washed mixture 29, to produce a washed stream 6.

In such cases, the installation 100 may comprise a washing section E comprising a mixing vessel 28 and a separation unit 30 comprising a decanter and/or a centrifuge.

The Optional Filtering Step f) and the Filtering Section

The process can comprise a filtering step f) comprising filtering the stream obtained in the previous step to obtain a filtered stream 7 wherein the filtering is performed to remove solids.

In the embodiments wherein the preceding step was the washing step e), the process may comprise a filtering step f) comprising filtering the washed stream 6 (i.e., the stream obtained in the previous step) to obtain a filtered stream 7 wherein the filtering is performed to remove solids from the washed stream 6, and/or to coalesce remaining traces of solvent if any.

In a preferred embodiment, the filtering comprises a first sub-step of filtering to remove solids and/or to coalesce remaining traces of solvent if any, preferably followed by a second sub-step of dewatering preferably using a molecular sieve to reach a water content of less than 0.1 vol. % preferably of less than 0.05% vol according to ASTM D95-13 (2018) on the filtered stream 7.

In such cases, the installation 100 may comprise a filtering section comprising a filter (not represented) and an optional molecular sieve 31.

The Separation Step q) and the Separation Section

The process comprises a step g) of performing a separation to separate the oligomeric product 33 from the purified liquified waste polymer 34.

In a preferred embodiment said step g) of separation is performed via distillation or steam distillation or vacuum stripping or fractional distillation or any combination.

Thus, the installation comprises a separation unit 32 comprising one or more distillation columns.

The oligomeric product 33 obtained can also be used further converted into valuable as valuable resins. After the separation step g), the oligomeric product 33 may be recovered and mixed with an elastomer, a curing agent, and a filler to obtain a rubber composition or is used as a tackifying resin and mixed with an elastomer to form an adhesive composition.

If not yet done in a pretreatment section, the process may comprise a step of separating and recovering a fraction having a boiling range higher than 350° C., preferably higher than 300° C. This fraction can be recovered from any of the purified liquified waste polymer 34, the filtered stream 7, the washed stream 6, the second product stream 5, the neutralized product stream 4, the first product stream 3, the dried feedstream, or the feed stream 1. The fraction having an initial boiling point of at least 350° C., preferably at least 300° C., can therefore be removed and sent into an FCC unit, or a hydrocracking unit, a coker, or a visbreaker or blending said fraction having a boiling range higher than 350° C. in crude oil or in a crude oil cut to be further refined.

With preference, after the separation step g), the purified liquified waste polymer 34 is recovered and blended in the fuel pool; with preference, the purified liquified waste polymer is separated in a naphtha cut having a boiling range of less than 150° C. and a diesel cut having a boiling range between 15° and 350° C. wherein said naphtha cut is incorporated in a naphtha pool, said diesel cut is incorporated in a diesel pool.

After the separation step g), the purified liquified waste polymer can be recovered and can be further treated either pure or diluted optional purification step h) to trap silicon and/or metals and/or phosphorous and/or halogenates over at least one trap to obtain a purified stream 8.

The Optional Purification Step h)

In the optional step h), purification may be performed over at least one trap 35. In a preferred embodiment, the trap 35 consists of silica gel, clays, alkaline or alkaline earth metal oxide, iron oxide, ion exchange resins, active carbon, active aluminum oxide, molecular sieves, and/or porous supports containing lamellar double hydroxide modified or not and silica gel, or any mixture thereof used in the fixed bed techniques known in the art.

The trap 35 is preferably operated at a temperature ranging from 20 to 100° C. and/or an LHSV between 1 to 10 $h^{-1}$, and/or a pressure ranging from 1 to 90 barg in the presence of $H_2$ or in the absence of $H_2$. The trap 35 is able to capture silicon and/or metals and/or phosphorous and/or halogenates, being preferably chosen among Ca Mg Hg via absorption and/or adsorption or it can also be constituted of one or more active guard beds with an adapted porosity. It can work with or without hydrogen coverage.

The trap 35 can be constituted of an adsorbent mass such as for instance a hydrated alumina. Molecular sieves can also be used to trap silicon. Other adsorbents can also be used such as silica gel for instance. The silicon trap is preferably able to trap organic silicon. Indeed, it is possible that the silicon present in the streams is in the form of organic silicon.

In a preferred embodiment, silicon and/or metals and/or phosphorous and/or halogenates are trapped with activated carbon. Activated carbon possesses preferably a high surface area (600-1600 $m^2/g$), and is preferably porous and hydrophobic in nature. Those properties lead to superior adsorption of non-polar molecules or little ionized molecules. Therefore, activated carbon can be used to reduce for instance siloxane from the liquid feed at temperatures from 20 to 150° C., at pressures from 1 to 100 bar, or from vaporized feed from 150 to 400° C. at pressure from 1 to 100 bar. Regeneration of saturated adsorbent can be performed via heating while using a sweeping gas.

In a preferred embodiment, silicon and/or metals and/or phosphorous and/or halogenates are trapped with silica or silica gel. Silica gel is an amorphous porous material, the molecular formula usually as $(SiO_2) \cdot nH_2O$, and unlike activated carbon, silica gel possesses polarity, which is more conducive to the adsorption of polar molecules. Because of —Si—O—Si— bonds, siloxanes exhibit partial polar character, which can contribute to adsorb on the silica gel surface. The adsorption force of silica gel is often weak enough allowing regeneration of silica gel by heat treatment above 150 up to 300° C. using a sweeping gas.

In a preferred embodiment, silicon and/or metals and/or phosphorous and/or halogenates are trapped with molecular sieves. Molecular sieves are hydrous aluminosilicate substances, with the chemical formula $Na_2O \cdot Al_2O_3 \cdot nSiO_2 \cdot xH_2O$, which possesses a structure of three-dimensional crystalline regular porous and ionic exchange ability. Compared with silica gel, molecular sieves favor adsorption of high polarity. The regeneration of exhausted absorbents can be achieved via heating at high temperatures to remove siloxane. Often, the regeneration is less efficient as the siloxanes might react irreversibly with the molecular sieve. In the most preferred embodiment, the molecular sieves are ion-exchanged or impregnated with a basic element such as Na. $Na_2O$ impregnation levels range from 3-10% wt. typically and the type of sieve is typically of the A or faujasite crystal structure.

In a preferred embodiment, silicon and/or metals and/or phosphorous and/or halogenates are trapped with activated aluminum oxide. Activated aluminum oxide possesses a large surface area (100-600 $m^2/g$), which shows a high affinity for siloxanes but also for polar oxide, organic acids, alkaline salts, and water. It can be an alkaline or alkaline-earth or rare-earth containing promoted alumina, the total weight content of these doping elements being less than 20% wt., the doping elements being preferably selected from Na, K, Ca, Mg, La, or mixture thereof. It can also be a metal-promoted alumina where the metal is selected from group VI-B metal with hydrogenating activity such as Mo, W, and/or from group VIII metal, such as Ni, Fe, Co.

In another embodiment, silicon and/or metals and/or phosphorous and/or halogenates are trapped with alkaline oxide. Alkaline oxide for high-temperature treatment such as calcium oxide (CaO) has strong activity to breakdown siloxanes and can be used as a non-regeneratable adsorbent at temperatures between 15° and 400° C.

In another embodiment, silicon and/or metals and/or phosphorous and/or halogenates are trapped with porous supports containing lamellar double hydroxides, being preferably hydrotalcite. The hydrotalcite can comprise one or more metals with hydrogenating capacity selected from group VIB or Group VIII, preferably Mo. Those metals can be supported on the surface of the hydrotalcite, or can have been added to the actual structure of the lamellar double hydroxide, in complete or partial substitution; as an example, but without limiting the scope of the present invention, the divalent metal, usually Mg, can be exchanged for Ni, or the trivalent metal, substituted by Fe instead of Al.

The above-mentioned traps 35 or solid adsorbents can be used alone or in combination in order to optimize the removal of silicon and/or metals and/or phosphorous and/or halogenates.

In another embodiment, silicon and/or metals and/or phosphorous and/or halogenates are trapped with a multi-layered guard bed comprising at least two layers wherein the layer on the top of the bed is selected from silica gel, clays, alkaline or alkaline earth metal oxide, iron oxide, ion exchange resins, active carbon, active aluminum oxide, molecular sieves and wherein the layer on the bottom of the bed is selected from silica gel, clays, alkaline or alkaline earth metal oxide, iron oxide, ion exchange resins, active carbon, active aluminum oxide, molecular sieves. More preferably said layer on the top of the guard bed comprises silica gel and/or active carbon and said layer on the bottom of the guard bed comprises molecular sieves and/or active aluminium oxide.

In another embodiment, when the liquified waste polymer contains high quantities of HCl and/or Halogenated compounds (namely at least 500 ppm wt. of HCl based on the total amount of liquified waste polymer), particular adsorbents can be used such as silica, clays—such as bentonite, hydrotalcite—alkaline or alkaline earth metal oxides—such as iron oxides, copper oxides, zinc oxide, sodium oxide, calcium oxide, magnesium oxide-alumina and alkaline or alkaline-earth promoted alumina-, iron oxide (hematite, magnetite, goethite), ion exchange resins or a combination thereof. In a most preferred embodiment, silicon and/or metals and/or phosphorous and/or halogenates containing at least 500 ppm wt. of HCl based on the total amount of liquified waste polymer are trapped with activated alumina. As HCl is a polar molecule, it interacts with polar sites on the alumina surface such as hydroxyl groups. The removal mechanism relies predominantly on physical adsorption and low temperature and the high alumina surface area is required to maximize the capacity for HCl removal. The HCl molecules remain physically adsorbed as a surface layer on the alumina and can be removed reversibly by hot purging. Promoted aluminas are hybrid in which a high alumina surface area has been impregnated with a basic metal oxide or similar salts, often of sodium or calcium. The alumina surface removes HCl through the mechanisms previously described, however, the promoter chemically reacts with the HCl giving an additional chloride removal mechanism referred to as chemical absorption. Using sodium oxide as an example of the promoter, the HCl is captured by the formation of sodium chloride. This chemical reaction is irreversible unlike physical adsorption and its rate is favored by higher temperatures. The promoted alumina chloride guards are very effective for liquid feeds due to their irreversible nature and high rate of chemical reaction once the HCl reaches the reactive site.

Another class of chemical absorbents combines Na, Zn, and Al oxides in which the first two react with HCl to form complex chloride phases, for example, $Na_2ZnCl_4$, and the chemical reactions are irreversible. U.S. Pat. Nos. 4,639,259 and 4,762,537 relate to the use of alumina-based sorbents for removing HCl from gas streams. U.S. Pat. Nos. 5,505,926 and 5,316,998 disclose a promoted alumina sorbent for removing HCl from liquid streams by incorporating an alkali metal oxide such as sodium in excess of 5% by weight onto an activated alumina base. Other Zn-based products range from the mixed metal oxide type composed of ZnO and $Na_2O$ and/or CaO. The rate of reaction is improved with an increase in reactor temperature for those basic (mixed) oxides.

In some embodiments, after the separation step g), the purified liquified waste polymer is recovered and is further treated either pure or diluted in one or more of the following steps:

h) an optional purification step to trap silicon and/or metals and/or phosphorous and/or halogenates over at least one trap 35 to obtain a purified stream 8;

i) an optional hydrotreating step of purified stream 8 or of said purified liquified waste polymer at a temperature of at least 200° C. to obtain a hydrotreated stream 9;

j) a steam cracking step of said hydrotreated stream 9 or of said purified stream 8 or of said purified liquified waste polymer to produce olefins such as ethylene and propylene and aromatics.

The Optional Hydrotreating Step

In the optional step i), a hydrotreatment step at a temperature of at least 200° C. is a preferred embodiment. The hydrotreatment step consists of a step at a temperature higher than 200° C., in the presence of hydrogen with well-known catalysts to hydrogenate the olefins and to convert hetero atoms such as sulfur, and nitrogen components into respectively $H_2S$ and $NH_3$. Depending on the composition of the stream entering this hydrotreating step, it is either performed in the gas phase or the reactor operates in trickle bed mode. This step can have also a metal trap function, a cracking function, and a de-aromatization function depending on the characteristic of the catalyst and the used operating condition. This step can be performed in one reactor with different layers of catalysts or several reactors in series depending on the function sought.

In a preferred embodiment, after said hydrotreating step, the concentration of olefins as measured via the bromine number in said purified hydrocarbon stream is at most 5.0, preferably at most 2.0 g $Br_2$/100 g, more preferably at most 1.5 g $Br_2$/100 g even more preferably at most 0.5 g $Br_2$/100 g as measured according to ASTM D1159-07(2017). Indeed, the hydroprocessing step i) leads to a reduced concentration of double bonds or reactive molecules. The purified liquified waste polymer obtained at step i) can directly be sent at least partially to a steam cracker with a reduced risk of coke formation.

In a preferred embodiment, said hydrotreating step is performed in one or more catalyst beds with preferably an overall temperature increase of at most 100° C. and/or a temperature increase of at most 50° C. over each catalyst bed, with preferably intermediary quench between said catalyst beds, said quench being preferably performed with H2 or with said purified liquified waste polymer recovered after said step i).

In a preferred embodiment, the inlet temperature of said hydrotreating step is at least 200° C. preferably 230° C., more preferably 250° C. and at most 500° C.

In another preferred embodiment, said hydrotreating step is performed at an LHSV between 1 to 10 $h^{-1}$, preferably 2 to 4 $h^{-1}$.

In another preferred embodiment, said hydrotreating step is performed at a pressure ranging from 10 to 90 barg in the presence of $H_2$.

In another preferred embodiment, said hydrotreating step is performed over a catalyst that comprises at least one metal of group VIB as for example Mo, W in combination or not with a promotor selected from at least one metal of group VIII and/or VIIIB as for example Ni and/or Co, and/or a mixture thereof, preferably these metals being used in the sulfided form and supported on alumina, titania, zirconia, silica, carbon and/or mixtures thereof.

In another preferred embodiment, said hydrotreating step is performed with a ratio H2/hydrocarbon ranging from 200 NL/L to 900 NL/L, preferably in the presence of at least 0.005 wt. %, preferably 0.05 wt. % even more preferably 0.5 wt. % of sulfur, preferably H2S or organic sulfur compounds, in the feedstream of said step i).

In another preferred embodiment, on the top of the said hydrotreatment, a silicon trap is present working at a temperature of at least 200° C., and/or an LHSV between 1 to 10 $h^{-1}$, and/or a pressure ranging from 10 to 90 barg in presence of $H_2$; optionally with a metal trap working at a temperature of at least 200° C., an LHSV between 1 to 10 $h^{-1}$, a pressure ranging from 10 to 90 barg in presence of $H_2$.

In another preferred embodiment, said hydrotreating step is performed over at least one catalyst that presents both (i) a hydrotreating function, namely at least one metal of group VIB as for example Mo, W in combination or not with a promotor selected from at least one metal of group VIII and/or VIIIB as for example Ni and/or Co, and/or a mixture thereof, preferably these metals being used in the sulfided form and (ii) a trap function, namely said catalyst presents a BET surface area ranging from 150 $m^2$/g to 400 $m^2$/g In another preferred embodiment, the stream entering the hydrotreating step is further diluted with any stream containing paraffins with the optional addition of a sulfur component, for instance, DMDS (dimethyl disulfur), so that the concentration of sulfur is of at least 0.005 wt. % of sulfur, preferably 0.05 wt. % of sulfur to at most 0.5 wt. %.

In another preferred embodiment, the effluent obtained after said hydrotreating step is further washed with water to remove inorganic compounds such as hydrosulphide, hydrogen chloride, ammonia, and ammonium salts and preferably further hydrocracked at a temperature of 350-430° C., a pressure of 30-180 barg, an LHSV of 0.5-4 $h^{-1}$, and/or under an $H_2$ to hydrocarbons ratio of 800-2000 NL:L to reduce the final boiling point of at least 10% prior to being sent at least partially to the steam cracker.

In a preferred embodiment, a guard bed to trap solid particles is located on the top of said hydrotreating step. In a preferred embodiment, the optional hydrotreating step can be performed on streams (6), (7) or (8) or any mixture of the washed stream (6), (7) or (8).

The Optional Steam Cracking Step and the Steam Cracking Section Including a Steam Cracker 37

In a preferred embodiment, the purified liquified waste polymer 34 or the purified stream 8 or the hydrotreated stream 9 obtained is sent to a steam cracker 37. The purified plastic oil may either be sent to the steam cracker without dilution. The purified plastic oil may also be mixed with naphtha, gasoil or crude oil to have a purified liquified waste polymer concentration ranging from 0.01 wt. % to at most 50 wt. %; preferably 0.1 wt. % to 25 wt. % even more preferably 1 wt. % to 20 wt. % at the inlet of the steam cracker. The purified liquified waste polymer 34 or the purified stream 8 or the hydrotreated stream 9 is then converted into olefins 38, such as ethylene and propylene, and also aromatics.

In a preferred embodiment, the purified liquified waste polymer 34 or the purified stream 8 or the hydrotreated stream 9 is sent at least partially directly to a steam cracker without further dilution and preferably as the only stream sent to the steam cracker 37, to produce mainly olefins 38, such as ethylene and propylene, and aromatics.

The steam cracker 37 is known per se in the art. The feedstock of the steam cracker in addition to the stream obtained via the inventive process can be ethane, liquefied petroleum gas, naphtha or gasoils, or crude oil. Liquefied petroleum gas (LPG) consists essentially of propane and butanes. Gasoils have a boiling range from about 200 to 350° C., consisting of C10 to C22 hydrocarbons, including essentially linear and branched paraffins, cyclic paraffins and aromatics (including mono-, naphtho- and poly-aromatic).

In particular, the cracking products obtained at the exit of the steam cracker may include ethylene, propylene, and benzene, and optionally hydrogen, toluene, xylenes, and 1,3-butadiene.

In a preferred embodiment, the outlet temperature of the steam cracker may range from 800 to 1200° C., preferably from 820 to 1100° C., more preferably from 830 to 950° C., more preferably from 840° C. to 920° C. The outlet temperature may influence the content of high-value chemicals in the cracking products produced by the present process.

In a preferred embodiment, the residence time in the steam cracker, through the radiation section of the reactor where the temperature is between 65° and 1200° C., may range from 0.005 to 0.5 seconds, preferably from 0.01 to 0.4 seconds.

In a preferred embodiment, steam cracking is done in the presence of steam in a ratio of 0.1 to 1.0 kg steam per kg of hydrocarbon feedstock, preferably from 0.25 to 0.7 kg steam per kg of hydrocarbon feedstock in the steam cracker, preferably in a ratio of 0.35 kg steam per kg of feedstock mixture, to obtain cracking products as defined above.

In a preferred embodiment, the reactor outlet pressure may range from 500 to 1500 mbars, preferably from 700 to 1000 mbars, and more preferably may be approx. 850 mbars. The residence time of the feed in the reactor and the temperature are to be considered together. A lower operating pressure results in easier light olefins formation and reduced coke formation. The lowest pressure possible is accomplished by (i) maintaining the output pressure of the reactor as close as possible to atmospheric pressure at the suction of the cracked gas compressor (ii) reducing the pressure of the hydrocarbons by dilution with steam (which has a substantial influence on slowing down coke formation). The steam/feedstock ratio may be maintained at a level sufficient to limit coke formation.

Effluent from the steam cracker contains unreacted feedstock, desired olefins (mainly ethylene and propylene), hydrogen, methane, a mixture of C4's (primarily isobutylene and butadiene), pyrolysis gasoline (aromatics in the C6 to C8 range), ethane, propane, di-olefins (acetylene, methyl acetylene, propadiene), and heavier hydrocarbons that boil in the temperature range of fuel oil (pyrolysis fuel oil). This cracked gas is rapidly quenched to 338-510° C. to stop the pyrolysis reactions, minimize consecutive reactions and recover the sensible heat in the gas by generating high-pressure steam in parallel transfer-line heat exchangers (TLE's). In gaseous feedstock-based plants, the TLE-quenched gas stream flows forward to a direct water quench tower, where the gas is cooled further with recirculating cold water. In liquid feedstock-based plants, a pre-fractionator precedes the water quench tower to condense and separate the fuel oil fraction from the cracked gas. In both types of plants, the major portions of the dilution steam and heavy gasoline in the cracked gas are condensed in the water quench tower at 35-40° C. The water-quench gas is subsequently compressed to about 25-35 Bars in 4 or 5 stages. Between compression stages, the condensed water and light gasoline are removed, and the cracked gas is washed with a caustic solution or with a regenerative amine solution, followed by a caustic solution, to remove acid gases ($CO_2$, $H_2S$, and $SO_2$). The compressed cracked gas is dried with a desiccant and cooled with propylene and ethylene refrigerants to cryogenic temperatures for the subsequent product fractionation: front-end demethanization, front-end depropanization or front-end deethanization.

The Optional Cracking Step k) and the Cracking Section 39

In a preferred embodiment, the purified liquified waste polymer 34 or the purified stream 8 is cracked on a catalyst being a 10 MR and/or 12 MR molecular sieve in step k).

In another preferred embodiment, said cracking is performed at a temperature ranging from 500 to 650° C., more preferably from 520 to 600° C., yet more preferably from 540 to 580° C., typically around 560° C. to 580° C.

In another preferred embodiment, the cracking reaction is performed in a fixed bed reactor, or a moving bed reactor or a fluidized bed reactor.

In another preferred embodiment, the LHSV ranges from 1 to 30 h$^{-1}$, preferably from 5 to 20 h$^{-1}$, more preferably from 5 to 15 h$^{-1}$.

In another preferred embodiment, the total pressure in the reactor ranges from 0.5 to 10 barg, preferably from 0.5 to 5 barg, more preferably from 0.5 to 2 barg; In another preferred embodiment, the cracking reaction is performed without hydrogen or hydrogen is present at a pressure of a maximum 2.5 barg, preferably at a pressure of a maximum of 1.5 barg; preferably in the presence of dimethyl disulfur at a concentration ranging from 50 to 300 ppm wt., more preferably at a concentration of 150 ppm wt.

In another preferred embodiment, the catalyst is selected from SAPO-5, and the like having an AFI structure, SAPO-41, and the like having an AFO structure, SAPO-11, and the like having an AEL structure, structure or SAPO-37, and the like having a FAU structure with preferably a silicon content ranging from 0.1 to 10 atom %, where the sum of Al+P+Si is 100, or MFI, for instance ZSM-5, silicalite-1, boralite C, TS-1; MEL, for instance ZSM-11, silicalite-2, boralite D, TS-2, SSZ-46; FER for instance Ferrierite, FU-9, ZSM-35; MTT for instance ZSM-23; MWW for instance MCM-22, PSH-3, ITQ-1, MCM-49; TON for instance ZSM-22, Theta-1, NU-10; EUO for instance ZSM-50, EU-1; MFS for instance ZSM-57; CON like CIT-1; and ZSM-48 family of microporous materials consisting of silicon, aluminium, oxygen and optionally boron; preferably the cracking catalyst is a crystalline silicate, metal containing crystalline silicate or a dealuminated crystalline silicate or any mixture thereof; most preferably the cracking catalyst has a MFI or the MEL structure advantageously modified with the metals Mg, Ca, La, Ni, Ce, Zn, Co, Ag, Fe, Cu, or Ga or mixtures thereof with a metal content preferably of at least 0.1 wt. % and at most 10 wt. %; preferably the cracking catalyst is a P-modified zeolite, Phosphorus-modified zeolite, preferably prepared based on MFI, MOR, MEL, clinoptilolite or FER, MWW, TON, EUO, MFS, and ZSM-48 family having an initial Si/Al ratio advantageously between 4 and 500

In another preferred embodiment, prior to said step k), a separation step k0) is performed so that the olefin content in the purified liquified waste polymer 34 or the purified stream 8 is of at most 60 wt. %, preferably at most 50 wt. %

In another preferred embodiment, after said step k), the olefins having 2 to 4 carbon atoms are recovered from the effluents 40 of said step k) simultaneously to a separation of gaseous effluents and with the separation of a fraction containing olefins having more than 4 carbon atoms, said olefins having more than 4 carbon atoms are recycled at the inlet of said step k) to be further cracked.

As regards the cracking catalyst of step k), it can be any acid catalyst capable to cause the cracking of the olefins and/or long-chain paraffins contained in the liquified waste polymer under above said conditions. The cracking catalyst preferably contains no noble metals. In particular, the olefin cracking catalyst preferably contains no Pt, no Pd, and no Au. By way of example, it can be molecular sieves, modified zeolites (including P-modified zeolites), a lamellar zeolite such as ITQ-2, metal-aluminophosphates. For example, a known catalyst may be used such as a solid acid catalyst e.g., a clay mineral such as kaolin, such as AI-MCM41, such as an aluminum phosphate The catalyst is employed under particular reaction conditions whereby the catalytic cracking of the C4+ olefins and/or C7+ paraffins readily proceeds. Different reaction pathways can occur on the catalyst. Catalytic cracking may be understood to comprise a process yielding shorter molecules via bond breakage.

In a preferred embodiment, the cracking catalyst is a crystalline Porous Aluminophosphate containing advantageously at least one 10 and/or 12 members ring into the structure.

The porous crystalline aluminophosphate may be one that is comprised of aluminum and phosphorus that are partly substituted by silicon, boron, Ni, Zn, Mg, and $M_n$ such as a porous crystalline metal aluminophosphate. The structure of such crystalline porous aluminophosphates may, for example, be those that are identified by codes for zeolites described above as AEL, AFI, AFO, or FAU.

The above porous crystalline aluminophosphate is preferably a porous crystalline silicoaluminophosphate. Specifically, SAPO5, and the like having an AFI structure, SAPO41, and the like having an AFO structure, SAPO11, and the like having an AEL structure, structure or SAPO37, and the like having a FAU structure may be mentioned.

According to another specific embodiment, suitable catalysts for the present process is the silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (where the sum of Al+P+Si is 100).

Various commercial zeolite products may be used, or it is possible to use zeolites that have been synthesized by a known method disclosed in the art.

According to a preferred embodiment, the cracking catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57), CON (CIT-1) and ZSM-48 family of microporous materials consisting of silicon, aluminum, oxygen and optionally boron. Advantageously the olefin cracking catalyst is a crystalline silicate, metal containing crystalline silicate, or a dealuminated crystalline silicate.

The crystalline silicate can have a ratio Si/Al of at least about 100 and is advantageously selected among the MFI and the MEL. The crystalline silicate can advantageously be modified with the metals Mg, Ca, La, Ni, Ce, Zn, Co, Ag, Fe, Cu, or Ga and mixtures thereof. In this latter case, the metal content is preferably at least 0.1 wt. %.

The dealuminated crystalline silicate is advantageous such as about 10% by weight of the aluminum is removed. Such dealumination is advantageously made by steaming optionally followed by leaching.

In another preferred embodiment the crystalline silicate catalyst is mixed with a binder, preferably an inorganic binder, and shaped to a desired shape, e.g., pellets. The binder is selected so as to be resistant to the temperature and other conditions employed in the process of the disclosure. The binder is an inorganic material selected from clays, silica, metal silicate, metal borates, metal oxides such as $ZrO_2$ and/or metals, or gels including mixtures of silica and metal oxides.

According to a preferred embodiment, the cracking catalyst is a P-modified zeolite (Phosphorus-modified zeolite). Said phosphorus-modified molecular sieves can be prepared based on MFI, MOR, MEL, clinoptilolite or FER, MWW, TON, EUO, MFS, and ZSM-48 family of microporous molecular sieves having an initial Si/Al ratio advantageously between 4 and 500. The P-modified zeolites of this recipe can be obtained based on cheap crystalline silicates with a low Si/Al ratio (below 30).

By way of example said P-modified zeolite is made by a process comprising in that order:

selecting a zeolite (advantageously with Si/Al ratio between 4 and 500) among $H^+$ or $NH_4^+$-form of MFI, MEL, FER, MOR, clinoptilolite, MWW, TON, EUO, MFS, and ZSM-48;

introducing P at conditions effective to introduce advantageously at least 0.05 wt. % of P;

separation of the solid from the liquid if any;

an optional washing step or an optional drying step or an optional drying step followed by a washing step;

a calcination step.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminum that leaves the zeolite framework and resides as aluminum oxides in and outside the pores of the zeolite. This transformation is known as dealumination of zeolites and this term will be used throughout the text. The treatment of the steamed zeolite with an acid solution results in dissolution of the extra-framework aluminum oxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911, 041, 5,573,990, and 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, $N_i$, Ce, Zn, Co, Ag, Fe, and Cu according to the recipe described in WO 09092779 and WO 09092781.

The separation of the liquid from the solid is advantageously made by filtering at a temperature between 0-90° C., centrifugation at a temperature between 0-90° C., and evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

The final equilibration step is performed advantageously at the temperature of 400-800° C. in the presence of steam for 0.01-48 h. Advantageously the steam partial pressure is at least 0.1 bars. Air, nitrogen, or any inert gases can be fed together with steam.

According to a preferred embodiment, the phosphorous-modified zeolite is made by a process comprising in that order:

selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS, and ZSM-48;

steaming at a temperature ranging from 400 to 870° C. for 0.01-200 h;

leaching with an aqueous acid solution at conditions effective to remove a substantial part of Al from the zeolite;

introducing P with an aqueous solution containing the source of P at conditions effective to introduce advantageously at least 0.05 wt. % of P;

separation of the solid from the liquid;

an optional washing step or an optional drying step or an optional drying step followed by a washing step;

a calcination step.

Optionally between the steaming step and the leaching step, there is an intermediate step such as, by way of example, contact with silica powder and drying.

Optionally the leaching and introducing P are made simultaneously by using an acid mixture comprising phosphorus to make the leaching.

Advantageously the selected MFI, MEL, FER, MOR, clinoptilolite, MWW, TON, EUO, MFS, and ZSM-48 (or $H^+$ or $NH_4^+$-form MFI, MEL, FER, MOR, clinoptilolite, MWW, TON, EUO, MFS, and ZSM-48) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt. % and preferably between 0.3 and 7 w %. Advantageously at least 10% of Al, with respect to parent zeolite MFI, MEL, FER, MOR, and clinoptilolite, MWW, TON, EUO, MFS, and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminum in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, 41thylenedi-aminetetraacetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g., the sodium or ammonium salts) or a mixture of two or more of such acids or salts.

The residual P-content is adjusted by P-concentration in the aqueous acid solution containing the source of P, drying conditions, and a washing procedure if any. A drying step can be envisaged between the filtering and washing steps.

Said P-modified zeolite can be used as itself as a catalyst. In another embodiment, it can be formulated into a catalyst by combining with other materials that provide additional hardness or catalytic activity to the finished catalyst product. Materials that can be blended with the P-modified zeolite can be various inert or catalytically active materials or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, or spheres, extruded into other shapes, or formed into spray-dried particles. The amount of P-modified zeolite which is contained in the final catalyst product ranges from 10 to 90 weight percent of the total catalyst, preferably 20 to 70 weight percent of the total catalyst.

The final equilibration step is performed advantageously at the temperature of 400-800° C. in the presence of steam for 0.01-48 h. Advantageously the steam partial pressure is at least 0.1 bars. Air, nitrogen, or any inert gases can be fed together with steam.

A possible catalyst for the olefin cracking is described in WO2009098262.

With regards to the operating conditions of step k), the cracking reaction can be performed in a fixed bed reactor, a moving bed reactor, or a fluidized bed reactor. A typical moving bed reactor is of the continuous catalytic reforming type. The process may also be performed continuously using a pair of parallel swing reactors.

The operating conditions of step k) are selected to disfavor hydrogen transfer reactions leading to the formation of paraffins, aromatics, and coke precursors. The operating conditions thus employ a high space velocity, a low pressure, and a high reaction temperature. Preferably, the LHSV ranges from 1 to 30 $h^{-1}$, preferably from 5 to 20 $h^{-1}$, and more preferably from 5 to 15 $h^{-1}$. The hydrocarbon feedstocks are preferably fed at a total inlet pressure sufficient to convey the feedstocks through the reactor. Preferably, the total pressure in the reactor ranges from 0.5 to 10 barg, preferably from 0.5 to 5 barg, and more preferably from 0.5 to 2 barg. The use of a low olefin partial pressure, for example, atmospheric pressure, tends to lower the incidence of hydrogen transfer reactions in the cracking process, which in turn reduces the potential for coke formation which tends to reduce catalyst stability. The cracking of the olefins and/or long chain paraffins is preferably performed at an inlet temperature of the feedstock of from 500 to 650° C., more preferably from 520 to 600° C., yet more preferably from 540 to 580° C., typically around 560° C. to 580° C. In accordance with a preferred aspect of the present disclosure, the hydrogen gas can be introduced into the olefin-containing feedstock preferably at a hydrogen partial pressure between 1 and 7.5 barg. Typically, the addition of hydrogen to the feedstock permits increasing the cycle time between successive regenerations of the catalyst. The inventive process is however advantaging in that the $H_2$ consumption stays very low if not null.

Detailed Description of the Polymerization Process (not Illustrated)

Upon exiting the steam cracking step j) or upon exiting the cracking step k), the cracked hydrocarbon stream is supplied to a separation unit. In the separation unit, a separation operation is performed to obtain mainly ethylene and propylene as well as other components such as aromatics, butadiene etc. It is preferred that the stream exiting the separation operation comprises 2 vol % to 99.9 vol % of ethylene or propylene, with regard to the total weight of the product exiting the separation operation. It is preferred that the product stream exiting the separation operation comprises 1000 ppm by vol. of the total of ethane and methane. It is preferred that the product stream exiting the separation operation comprises 5 ppm by vol. of oxygen. Such high purity is required to enable subsequent polymerization to be performed without disturbance of the polymerization process.

Subsequent to the separation operation, the obtained product stream is supplied to a polymerization reactor. In such a polymerization reactor, a polymerization reaction is performed to obtain ethylene-based polymers and respectively propylene-based polymers.

The polymerization reaction may be a solution polymerization reaction, a gas-phase polymerization reaction, a slurry polymerization reaction, or a free-radical polymerization reaction. In a particular embodiment, the polymerization reaction of step is a gas-phase polymerization process. Such a gas-phase polymerization process may be performed in the presence of a catalyst system for the polymerization of ethylene or propylene. Such catalyst system may for example be a Ziegler-Natta type catalyst system, a single-site type catalyst system such as a metallocene-type catalyst system, a chromium-type catalyst system, or any other catalyst system known in the art that is suitable for polymerization of ethylene in a gas-phase process.

Such a gas-phase polymerization process may be a homo-polymerization process or a co-polymerization process. For example, 1-butene, 4-methyl-1-pentene, 1-hexene, or 1-octene may be used as co-monomers in such copolymerization process.

A fluidized-bed polymerization may be used for the polymerization reaction of the present invention as a particular gas-phase polymerization process. In such a process, the formed polyethylene particles are maintained in a fluidized state by the upwards flow of the reactant gases, comprising ethylene, during the time that the reaction takes place, wherein once the particles are concluded to have reached the desired degree of polymerization, they are evacuated from the reactor together with the gaseous medium which is subsequently separated from the formed particles and recycled as a reactant, together with a make-up stream to compensate the reactant consumption.

Such a fluidized-bed process is particularly desirable as it allows for the polymerization of ethylene at relatively moderate levels of energy consumption, combined with a relatively moderate capital investment that is required.

Accordingly, the use of a fluidized-bed gas-phase polymerization process for the polymerization reaction of the present process may contribute to the overall carbon efficiency of the process of the invention as a result of the reduced energy requirements.

In a particular embodiment, the invention relates to a free-radical polymerization reaction. Such free-radical polymerization reaction involves the reaction of the product exiting the separation operation at a pressure of 2 to 100 MPa, preferably 2 to 150 MPa, more preferably 2 to 200 MPa, and even more preferably 2 to 225 MPa. Such free-radical polymerization reaction involves the reaction of the product exiting the separation operation at a pressure of 350 MPa, preferably 325 MPa, more preferably 300 MPa, and even more preferably 275 MPa. Such free-radical polymerization may for example be performed in the presence of a free-radical reaction initiator, such as a peroxide.

Such free-radical polymerization reaction may for example be performed in an autoclave reactor vessel or alternatively in a tubular reaction vessel, wherein the product exiting the separation operation is supplied to an inlet at the first end of the tubular vessel, and a product stream comprising the polymeric product is evacuated from an outlet at the second end of the tubular vessel.

The Oligomeric Product Recovered after the Step g)

The oligomeric product is liquid at ambient temperature.

In some embodiments, the oligomeric product shows an olefinic content of at most 20.0 wt. % as determined by $^1$H NMR. With preference, the liquid resin an olefinic content ranging from 0.1 to 20.0 wt. %; preferably from 0.3 to 15.0 wt. %; more preferably, from 0.5 to 10.0 wt. %. from 0.8 to 5.0 wt. %.

In some embodiments, the oligomeric product shows an aliphatic content ranging from 15 to 100 wt. % as determined by $^1$H NMR; preferably ranging from 40.0 to 99.5 wt. %; more preferably ranging from 50.0 to 99.0 wt. %; even more preferably ranging from 70.0 to 98.5 wt. %; and most preferably ranging from 80.0 to 98.0 wt. %.

In one or more embodiments, the oligomeric product shows an aromatic content ranging from 0.3 to 45.0 wt. % as determined by $^1$H NMR; preferably ranging from 0.5 to 40.0 wt. %; more preferably ranging from 0.8 to 30.0 wt. %; and even more preferably ranging from 1.0 to 20.0 wt. %.

In embodiments, the oligomeric product has viscosity at 30° C. ranging from 10 to 50 000 cps measured using a Brookfield viscometer; preferably ranging from 10 to 50 000 cps; more ranging from 10 to 10 000 cps; even more preferably ranging from 10 to 4 000 cps; and most preferably ranging from 10 to 2 500 cps.

In some embodiments, the oligomeric product has a number average molecular weight ($M_n$) ranging from 100 to 10,000 g/mol measured using gel permeation chromatography and a polystyrene calibration; preferably from 120 to 5,000 g/mol; more preferably from 140 to 1,000 g/mol; even more preferably from 150 to 800 g/mol; most preferably from 180 to 700 g/mol; or from 200 to 650 g/mol; or from 250 to 550 g/mol.

In some embodiments, the oligomeric product has a weight average molecular weight (Mw) ranging from 100 to 10,000 g/mol measured using gel permeation chromatography and a polystyrene calibration; preferably from 120 to 5,000 g/mol; more preferably from 150 to 3,500 g/mol; and even more preferably from 200 to 2,000 g/mol.

In some embodiments, the oligomeric product has a z-average molecular weight ($M_z$) ranging from 100 to 100,000 g/mol measured using gel permeation chromatography and a polystyrene calibration; preferably from 120 to 85,000 g/mol; more preferably from 150 to 70,000 g/mol; and even more preferably from 200 to 50,000 g/mol.

In some embodiments, the oligomeric product has a Mw/M$_n$ ranging from 1.0 to 10.0; preferably from 1.0 to 5.0; more preferably from 1.0 to 4.0; and even more preferably from 1.1 to 2.8.

In a preferred embodiment, the oligomeric product comprises a comonomer selected from the group consisting of styrene, alpha-methyl styrene, 2-methyl styrene, 3-methyl styrene, 4-methyl styrene, 4-t-butyl styrene, 4-cyclohexyl styrene, 4-dodecyl styrene, 2,4-diisopropyl styrene, 2,4,6-trimethyl styrene, 2-ethyl-4-benzylstyrene, 4-(phenylbutyl) styrene, 1-vinyl naphthalene, 2-vinyl naphthalene, vinyl anthracene, 4-methoxy styrene, monochlorostyrene, dichlorostyrene, divinyl benzene, Indene, methyl-Indene, and mixtures thereof; with preference the liquid resin (i.e., the oligomeric product) comprises a comonomer being or comprising styrene.

In embodiments, oligomeric product comprises a comonomer present at a concentration ranging from 0.01 to 90 mol. % based on the total weight of the liquid resin, preferably from 1.0 to 80 mol. %.

In some embodiments, the oligomeric product is a wax and/or shows a crystallisation temperature (Tc) below 35° C.; preferably ranging from 18 to 32° C.; more preferably ranging from 20 to 30° C.; and even more preferably ranging from 21 to 29° C.

In embodiments, the oligomeric product is a resin and/or shows a glass transition temperature (Tg) below −20° C. as determined by Differential Scanning calorimetry; preferably ranging from −60° C. to −25° C.; more preferably from −50° C. to −30° C.; and even more preferably from −49° C. to −35° C.

EXAMPLES

The Method Used for Measuring the Diene Content

Unless otherwise specified, the following method was used to determine the content of dienes in the pyrolysis plastic oils in all the examples.

The determination of the diene content is performed with the help of the GPC with a UV detector. A given quantity of maleic anhydride is added in the pyrolysis plastic oil and let to react with the dienes via the Diels-Alder reaction. The reduction of the UV active MA peak in the chromatograph is monitored and used to determine diene concentration. In a first step, a calibration curve is prepared. The equipment used are Agilent 1260 Series Degasser (Part Number G1322A); Agilent 1260 Series Isocratic Pump (Part Number G1310B); Agilent 1260 Series Autosampler (Part Number G1329B); Agilent 1260 Series Thermostatted Column Compartment (Part Number G1316A); Agilent 1260 Series Multiple Wavelength Detector (Part Number G1365C); and Agilent 1260 Series Refractive Index Detector (Part Number G1362A).

Column set: 1× Agilent ResiPore 50×4.6 mm Guard Column (Part Number PL1513-1300); and 2× Agilent ResiPore 250×4.6 mm 3 um Particle Size Columns (Part Number PL1513-5300).

Software: Cirrus 3.3, ChemStation B04.03[52].

Solvent: THF Stabilized with 250 ppm BHT Flow Rate: 0.45 ml/min.

Column Compartment Temperature: 40° C.

Calibration: polystyrene standards from Agilent EasiCal Standards i) GPC-UV Calibration of Maleic Anhydride:

Samples of known concentration of maleic anhydride (MA) in THF were prepared and analyzed using GPC with a UV detector.

The chromatograph at 240 nm was analyzed for peak area.

A plot of MA (ppm) versus peak area creates the calibration curve (FIG. 2). The equation of the line can be used to determine the concentration of MA in unknown solutions.

ii) Preparation of Samples for Testing:

A solution of 6% wt. maleic anhydride in toluene is prepared.

15 g of MA is added to 200 mL toluene and heated to 55° C. for 4 hours. The solution is then cooled, and the volume is brought to 250 mL.

The solution is let sit overnight and filtered the following day. This will remove some undissolved MA that has precipitated out.

Once made, the solution should be used within two weeks.

The concentration of the MA solution is checked using the equation from the GPC-UV calibration in the following (Equation 1.):

$$\frac{\left(\dfrac{0.1586 \times PA + 0.3095}{sample\ M.F.}\right)}{\left(\dfrac{Inj.\ Vol.}{5}\right)} = [MA](ppm) \qquad \text{Eq. 1}$$

where PA is the peak area (15.8-16.6 min) at 240 nm (mV·s), sample M.F is the concentration of the sample $$\left(\frac{sample\ (g)}{sample\ (g) + THF(g)}\right),$$

and Inj. Vol is the sample injection volume (uL). The equation 0.1586x+0.3095 is the equation of the line from the MA calibration plot.

iii) Preparation of Sample and Diels-Alder (D-A) Reaction.

Weight out 15 g of sample (pyrolysis oil) and add to a 100 mL round bottom flask (RBF).

Add 20 mL of the 6% MA in toluene solution and a stir bar to the 100 mL RBF with the sample.

Mix the solution gently then remove 55-70 mg of the mixture and place into 20 mL vial. Record the exact amount of mixture added.

Add 9-10 g of THF to the 20 mL vial recording the exact amount of THF added.

The sample in THF in the 20 mL vial will be used for the initial determination of MA for the diene calculation. Notated as initial in calculations. Run GPC-UV.

The mixture in the 100 mL RBF is then heated to reflux for 3 hours.

Upon refluxing, 55-70 mg of the solution is then placed into a second 20 mL vial. Record the exact amount added.

Add 9-10 g of THF to this second 20 mL vial recording the exact amount of THF added. This sample is used for the final determination of MA for the diene calculations. Notated as final in calculations. Run GPC-UV.

Determining amount of reacted and unreacted MA.

The initial amount of MA is calculated using equation 1 and the initial sample.

The final amount of MA is calculated using equation 1 and the final sample.

The results are converted from ppm to % and the amount of MA consumed is calculated using Equation 2:

$$1 - \frac{\text{Final } MA \text{ \%}}{\text{Initial } MA \text{ \%}} = MA \text{ consumed} \qquad \text{Eq. 2}$$

Determining the Diene % of the Sample.

To determine the diene content, it is needed to know the amount (g) of MA used during D-A reaction.

20 mL of 6% MA in toluene=1.8 g MA and 16.3 g toluene

Determine the percentage of C5H8 dienes and higher MW dienes.

Integration of the 240 nm peak area from 13.5-16 min and 16-18.5 min of the pure sample from GPC-UV gives the peak area percentages of the higher Mw dienes and the C5H8 dienes, respectively.

The Mw (g/mol) of the higher Mw dienes is determined using the Mw (g/mol) from the GPC and normalizing it using the Mw of the C5H8 peak and 68 g/mol.

Use Equation 3 to determine the diene percentage.

$$\left[\frac{\left(\frac{\text{g } MA \times \% \ C_5H_8 \times MA \ \text{Consumed}}{\text{Mw of } MA\left(\frac{g}{\text{mol}}\right)}\right) \times Mw \ C_5H_8\left(\frac{g}{\text{mol}}\right)}{\text{grams of pyrolysis oil sample}}\right] + \qquad \text{Eq. 3}$$

$$\left[\frac{\left(\frac{\text{g } MA \times \% \ \text{other dienes} \times MA \ \text{Consumed}}{\text{Mw of } MA\left(\frac{g}{\text{mol}}\right)}\right) \times Mw \ \text{other dienes}\left(\frac{g}{\text{mol}}\right)}{\text{grams of pyrolysis oil sample}}\right]$$

Details about the Pyrolysis Oil Used

The following pyrolysis plastic oils were used in the examples: Pyrolysis Oil 1: it has a boiling point ranging from 50° C. to about 480° C. and a Diene value of about 2.7%. The chlorine content is in the range of about 115 ppm, the silicium content is expected in the range of about 15 ppm. The oxygen content is expected in the range of about 1 wt. %. The nitrogen is expected in the range of about 1150 ppm wt.

Pyrolysis Oil 2: A light cut obtained by distillation of a pyrolysis oil (issued from a non-catalytic pyrolysis of mixed waste plastic) and having a boiling point ranging from about 50° C. to about 260° C. The water is expected to be below 100 ppm weight. The Diene value is expected to be in the range of about 4.8%.

Pyrolysis Oil 3: A light cut of non-catalytic pyrolysis plastic oil (obtained by staged condensation of the pyrolysis effluent) and having a boiling point ranging from <36° C. to about 260° C. This oil has been decanted to assure a water content below 100 ppm weight. The Diene value is expected to be in the range of about 7.8%.

Pyrolysis Oil 4: it has a boiling point ranging from 40° C. to about 401° C. and a Diene value of about 2.1%. The chlorine content is expected in the range of about 270 ppm, the silicium content is expected in the range of about 12 ppm. The oxygen content is expected in the range of about 0.3 wt. %. The nitrogen is expected in the range of about 1250 ppm wt.

Example 1. Purification Using BF₃

The purification of pyrolysis oil was prepared through solution polymerization wherein the catalyst and monomers were continuously fed into the reaction vessel and boron trifluoride diethyl etherate is used as the catalyst with the BF₃ weight percentage on the total feed being 1.15+/+ 0.25%.

The flow rate of the monomer feed and the Friedel-Craft catalyst is controlled so that the catalyst feed is about 2 to 3 wt. % on the combined mass flow of the monomer. The reaction temperature was maintained at 40° C. throughout the polymerization process and all steps carried out under a nitrogen blanket.

An initial amount of pyrolysis oil (~10 wt. % of the total) was added as the reaction heel to a round bottom flask (RBF) purged with nitrogen. The heel was then warmed to 40° C. while stirring under nitrogen. The pyrolysis oil feed and Lewis acid catalyst (BF₃—OEt₂) were each measured out in individual flasks. If a comonomer was used (i.e. styrene) it was measured out and added to the flask with the pyrolysis oil feed. The pyrolysis oil and catalyst were fed into the reactor while maintain a temperature of 40° C. so that the catalyst was added at 2 to 3 wt. % of the monomer and the two feeds finish adding at roughly the same time. Upon completion of the feed additions, the mixture was stirred at 40° C. for 45-60 minutes before cooling to room temperature. The polymerization was carried out under a nitrogen blanket.

The reaction mixture was then transferred to a separatory funnel and washed three times with ~0.1M NH₄OH, discarding the aqueous phase. The organic mixture was then washed twice more with water and the organic phase transferred to a separate three neck round bottom flask for distillation. During the washings, there is an insoluble tarry like residue that remains on the sides of the reaction flask and separatory funnel. In all cases of purification, the tarry residue was left behind unless otherwise noted.

The organic mixture was purged with nitrogen while being heated to 230° C. and the volatile organics were collected. Once the temperature reached 230° C. the distillation continued until there were no more volatiles being distilled at which point the nitrogen was replaced by steam. The volatiles collected prior to steam stripping are referred to as the distillate. Oligomeric product and steam condensate were collected until there was minimal oligomeric product being collected. The oligomeric product collected is referred to as oily polymer. The material remaining after steam stripping is a resin/wax product polymerized during purification. The distillate collected is the purified pyrolysis oil with the dienes reduced.

Table 2 shows the catalyst and comonomer amounts used for polymerization and the final diene concentration of the distillate following purification. The diene content has been reduced to less than 0.5% in all cases and in some instances, removed to undetectable levels, following polymerization.

TABLE 1

| | Poly 1 | Poly 2 | Poly 3 | Poly 4 | Poly 5 |
|---|---|---|---|---|---|
| Origin of the pyrolysis oil | Py Oil 1 | Py Oil 2 | Py Oil 2 | Py Oil 3 | Py Oil 3 |
| Initial Diene Percent | 2.7 | 4.8 | 4.8 | 7.8 | 7.8 |
| Styrene (wt. %) | — | — | 1.4 | — | 9.0 |
| BF3, wt. % (on total feed) | 0.92 | 1.16 | 1.24 | 1.40 | 1.28 |
| Final Diene Percent | 0.4 | 0.0 | 0.3 | 0.2 | 0.0 |

*Initial and final diene concentration.*

Example 2. Purification Using Aluminum Chloride (AlCl₃) as Catalyst

Hexanes (~10 wt. % of the total) were added to an RBF purged with nitrogen. The AlCl$_3$ catalyst, approximately 1.25 wt. % of the total feed, was then added to the hexanes and warmed to 35° C. while stirring under nitrogen. The pyrolysis oil feed was measured out in an individual flask and fed at a rate of 2 mL/min. Upon completion of the feed addition, the mixture was stirred at 35° C. for 50 minutes before cooling to room temperature. The polymerization was carried out under a nitrogen blanket.

The reaction mixture was then transferred to a separatory funnel and washed three times 25% aqueous isopropanol (IPA), discarding the aqueous phase. The organic mixture was then washed twice more with water and the organic phase was transferred to a separate three-neck round bottom flask for distillation. The organic mixture was then distilled, and steam stripped as in example 1.

Example 3. Purification Using Amberlyst 15 as the Catalyst

Pyrolysis oil was added to an RBF and stirred under nitrogen while warming to 40° C. Amberlyst 15, approximately 1 wt. % of the total feed, was added as the catalyst in two doses. The initial amount of Amberlyst 15 catalyst (⅔ of the total) was added once the oil reached 40° C. and then stirred at 40° C. for 45 minutes under nitrogen. The remaining ⅓ of catalyst was then added and the reaction was stirred for an additional 75 minutes. The mixture was then cooled to room temperature and the catalyst filtered. The organic mixture was then distilled, and steam stripped as in example 1.

Example 4. Purification Using Sulfuric Acid (H2SO4)

Pyrolysis oil was added to an RBF and stirred at room temperature. Sulfuric acid, approximately 2.5 wt. % on total feed, was then added to the stirring pyrolysis oil and there was an immediate exotherm. The reaction was stirred until the temperature dropped back to room temperature. The acid was neutralized, and the oil was washed with dilute sodium carbonate (2×) followed by water (2×). The oil was then distilled, and steam stripped as in example 1.

The next table summarizes the various amounts of Lewis Acid Catalyst used in examples 2 to 4.

TABLE 2

| | AlCl₃ | Amberlyst 15 | Sulfuric Acid |
|---|---|---|---|
| Hexanes (g) | 8.5 | — | — |
| Catalyst (g) | 0.95 | 0.84 | 1.25 |
| Py Oil 3 (g) | 75.6 | 86.2 | 63.8 |

*Summary of the Lewis Acid catalyst quantities used.*

Figure 3:
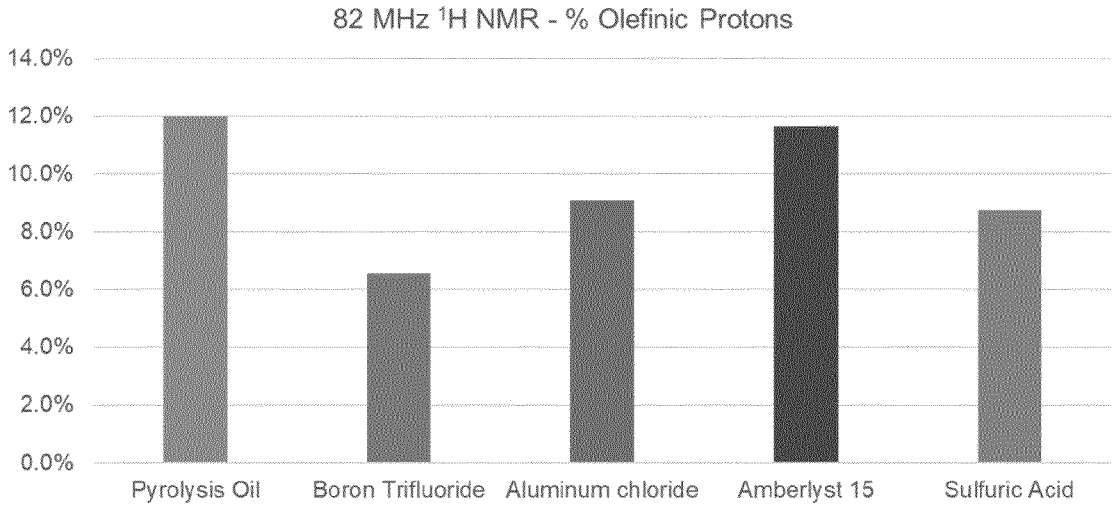
FIG. 3 describes the ${}^1$H NMR olefinic content of treated pyrolysis oil compared to crude pyrolysis oil according to examples 2 to 4.
Figure 4:
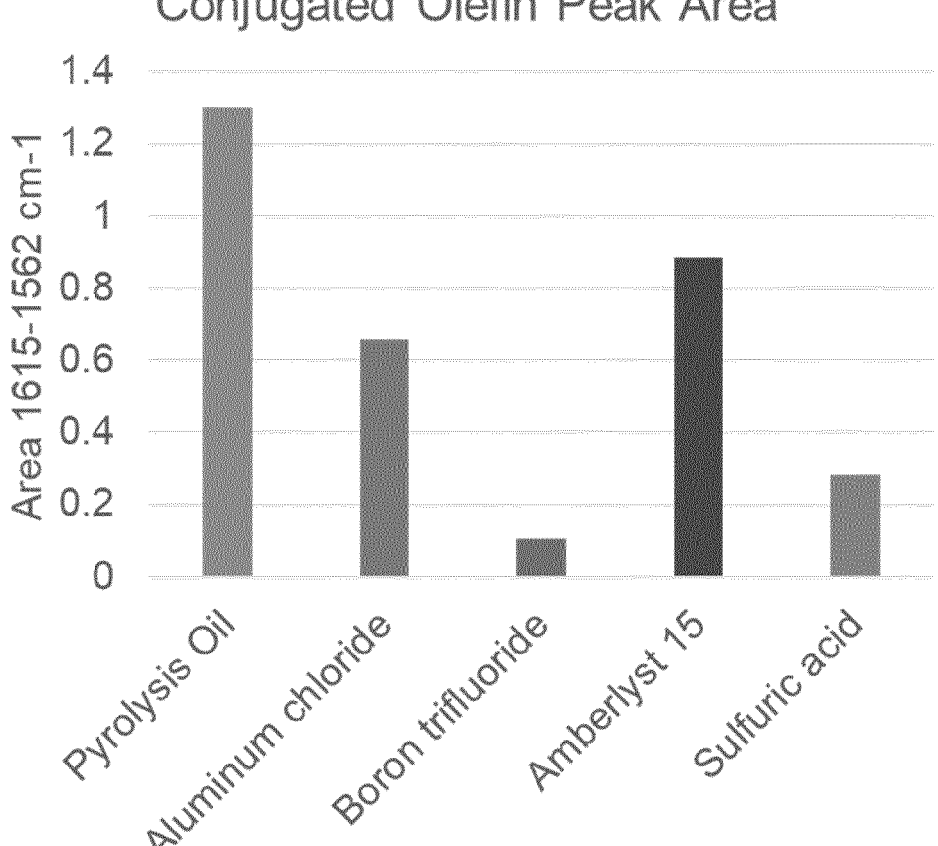
FIG. 4 describes olefinic carbon stretching peak areas from FTIR obtained on examples 2 to 4.

For examples 2 to 4, the impact of the purification process via cationic polymerization was measured via 82 MHz $^1$H NMR and FTIR as presented respectively in FIGS. 2 and 3. The comparison of the fraction attributed to olefinic protons in the pyrolysis oil with the same fraction after cationic polymerization shows a decrease in the fraction of olefinic protons with all acid catalysts used. A similar conclusion arises from FIG. 3 where the conjugated olefin peak area decreases with the cationic polymerization. Examples 2 to 4, therefore, demonstrate that the cationic polymerization allows reducing the diene content with the catalyst AlCl$_3$, Amberlyst 15 and sulfuric acid.

The invention claimed is:

1. Process for the purification of a liquified waste polymer comprising the following steps:
   a) providing a feedstream (1) containing liquified waste polymer, wherein said feedstream (1) contains at least 0.1 wt. % to at most 80 wt. % of dienes based on the total weight of said feedstream (1);
   c) performing a polymerization reaction on said feedstream (1) under polymerization conditions to obtain a first product stream (3) comprising an oligomeric product (33), wherein the polymerization reaction is a cationic polymerization performed in the presence of an acidic catalyst;
   d) optionally, performing a neutralization reaction by contacting said first product stream (3) with a basic compound (25) to obtain a neutralized product stream (4) and removing said basic compound from neutralized product stream (4) to obtain a second product stream (5);
   g) performing a separation to separate the oligomeric product (33) from the liquified waste polymers to obtain a purified liquified waste polymer (34).

2. The process according to claim 1 is characterized in that the process further comprises a step (b) of drying the feedstream (1) to obtain a dried feedstream (2) wherein the step b) is performed before the step c) of polymerization so that the step c) of the polymerization reaction is performed on the dried feedstream (2).

3. The process according to claim 2 is characterized in that step b) of drying is performed and comprises a sub-step b1) of decantation and/or centrifugation; with preference, the first sub-step b1) is followed by a second sub-step b2) of drying using a molecular sieve to reach a water content of less than 0.1 vol. % according to ASTM D95-13 (2018).

4. The process according to claim 1 is characterized in that the acidic catalyst is a Brönsted acid or a Lewis acid.

5. The process according to claim 1 is characterized in that the polymerization reaction in step c) is a cationic polymerization performed in the presence of an acidic catalyst being a Lewis acid chosen among BF$_3$, complexes of boron trifluoride, AlCl$_3$, SnC$_{14}$, ZnCl$_2$, FeCl$_3$ and TiCl$_3$, alkyl aluminum chlorides, H$_2$SO$_4$ or any mixture thereof; with preference, acidic catalyst is or comprises boron trifluoride etherate.

6. The process according to claim 1 is characterized in that the polymerization reaction of step c) is performed in the presence of one or more comonomers; with preference, the one or more comonomers comprise a vinyl aromatic and/or the one or more comonomer are present at a concentration from 1.0 to 25.0 wt. % based on the total weight of the liquified waste polymer.

7. The process according to claim 1 is characterized in that step d) is performed and in that the basic compound:

has a pKa in water ranging from 7.5 to 14; and/or is selected from LiOH, NaOH, CsOH, Ba(OH)$_2$, Na$_2$O, KOH, K$_2$O, CaO, Ca(OH)$_2$, MgO, Mg(OH)$_2$, NH$_4$OH or any mixtures thereof.

8. The process according to claim 1 is characterized in that step d) is performed in continuous mode and/or in that step d) performed and the removal of said basic compound from neutralized product stream (4) to obtain a second product stream (5), is performed by decantation and/or by centrifugation.

9. The process according to claim 1 is characterized in that it further comprises a step f) of filtering the stream obtained in the previous step to obtain a filtered stream (7) wherein the filtering is performed to remove solids from the first product stream (3) or from the second product stream (5) or from the washed stream (6), and/or to coalesce remaining traces of solvent if any; with preference, the filtering step is followed by a dewatering step.

10. The process according to claim 1 is characterized in that step g) of separation is performed via distillation or steam distillation or vacuum stripping or fractional distillation or any combination.

11. The process according to claim 1 is characterized in that, after the separation step g), the oligomeric product (33) is recovered and mixed with an elastomer, a curing agent, and a filler to obtain a rubber composition or is used as a tackifying resin and mixed with an elastomer to form an adhesive composition.

12. The process according to claim 1 is characterized in that, after the separation step g), the purified liquified waste polymer is recovered and blended in the fuel pool; with preference, the purified liquified waste polymer is separated in a naphtha cut having a boiling range of less than 150° C. and a diesel cut having a boiling range between 15° and 350° C. wherein said naphtha cut is incorporated in a naphtha pool, said diesel cut is incorporated in a diesel pool.

13. The process according to claim 1 is characterized in that, after the separation step g), the purified liquified waste polymer is recovered and is further treated either pure or diluted in one or more of the following steps:

h) an optional purification step to trap silicon and/or metals and/or phosphorous and/or halogenates over at least one trap (35) to obtain a purified stream (8); and/or i) an optional hydrotreating step of the purified stream (8) or of said purified liquified waste polymer at a temperature of at least 200° C. to obtain a hydrotreated stream (9);

j) a steam cracking step of said hydrotreated stream (9) or of said purified stream (8) or of said purified liquified waste polymer to produce olefins such as ethylene and propylene and aromatics.

14. The process according to claim 1 is characterized in that, after the separation step g), the purified liquified waste polymer is recovered and is further treated either pure or diluted in one or more of the following steps:

h) an optional purification step to trap silicon and/or metals and/or phosphorous and/or halogenates over at least one trap to obtain a purified stream (8); and/or k) a cracking step wherein said purified liquified waste polymer or said purified stream (8) being preferably diluted with a diluent, is cracked on a catalyst being a 10 MR or 12 MR molecular sieve at a temperature ranging from 450° C. to 650° C., a total pressure ranging from 0.5 to 10 barg and/or with a hydrogen partial pressure ranging from 0 to 7.5 barg to crack the olefins and/or paraffins of said purified liquified waste polymer into olefins having 2 to 4 carbon atoms.

15. The process according to claim 1 is characterized in that the liquified waste polymer is a pyrolysis plastic oil, with preference, the step a) of providing a feedstream (1) containing liquified waste polymer comprises the preliminary steps of preparation of liquified waste polymer including:

a1) of providing a waste plastics stream;

a2) pyrolyzing said waste plastics stream at a temperature of at least 200° C.;

a3) recovering a pyrolizer effluent and separating, into a C$_1$ to C$_4$ hydrocarbons fraction, a fraction having a boiling range higher than 350° C. and a remaining fraction being said pyrolysis plastic oil;

a4) optionally sending the fraction having a boiling range higher than 350° C. into a Fluid Catalytic Cracking unit, or a hydrocracking unit, a coker or a visbreaker or blending said fraction having a boiling range higher than 350° C. in crude oil or in a crude oil cut to be further refined.

16. The process according to claim 1 is characterized in that the liquified waste polymer in the feedstream (1) has a final boiling point of at most 700° C. and/or feedstream (1) contains from 0.1 to 50.0 wt. % of dienes based on the total weight of said feedstream (1).

\* \* \* \* \*